United States Patent
Yoon et al.

(10) Patent No.: US 11,295,868 B2
(45) Date of Patent: Apr. 5, 2022

(54) SYSTEM AND METHOD FOR ASSESSING PHYSICAL ACTIVITY LEVEL USING HEALTH DATA FROM USER COMPUTING DEVICES

(71) Applicant: Kinesiometrics, Inc., North Miami, FL (US)

(72) Inventors: Jang W. Yoon, Philadelphia, PA (US); Gregory W. Basil, Miami, FL (US); Michael Y. Wang, North Miami, FL (US)

(73) Assignee: KINESIOMETRICS, INC., North Miami, FL (US)

( * ) Notice: Subject to any disclaimer, the term of this patent is extended or adjusted under 35 U.S.C. 154(b) by 0 days.

(21) Appl. No.: 17/303,830

(22) Filed: Jun. 8, 2021

(65) Prior Publication Data

US 2021/0383933 A1 Dec. 9, 2021

Related U.S. Application Data

(60) Provisional application No. 63/036,299, filed on Jun. 8, 2020.

(51) Int. Cl.
*G16H 50/70* (2018.01)
(52) U.S. Cl.
CPC .................................. *G16H 50/70* (2018.01)
(58) Field of Classification Search
CPC ..................................................... G16H 50/70
See application file for complete search history.

(56) References Cited

U.S. PATENT DOCUMENTS

| | | | |
|---|---|---|---|
| 2015/0019241 A1* | 1/2015 | Bennett | G16H 50/20 705/2 |
| 2015/0193583 A1* | 7/2015 | McNair | G16H 50/20 705/2 |

(Continued)

OTHER PUBLICATIONS

International Search Report and Written Opinion of corresponding PCT Application No. PCT/US2021/036457—21 pages (dated Sep. 21, 2021).

(Continued)

*Primary Examiner* — Michael Tomaszewski
*Assistant Examiner* — Jay M. Patel
(74) *Attorney, Agent, or Firm* — Knobbe Martens Olson & Bear, LLP

(57) ABSTRACT

Generally described, one or more aspects of the present application relate to enabling determination of a predicted surgical efficacy of a proposed surgical intervention and a predicted pattern of post-operative recovery for the patient. More specifically, the present disclosure provides a system that can analyze the patient data of a plurality of patients data, generate analytics data indicating the post-operative recovery of the plurality of patients, and store the analytics data in association with the biological traits of the patients and the types of surgical interventions that the patients had. Subsequently, the system can analyze the patient traits and activity data of a patient, and output, based on the previously generated analytics data, a prediction of how efficacious a given surgical intervention might be for that patient and/or how the patient might recover from the given surgical intervention.

20 Claims, 19 Drawing Sheets

(56) References Cited

U.S. PATENT DOCUMENTS

| | | | |
|---|---|---|---|
| 2015/0227710 A1* | 8/2015 | Pappada | G16H 70/20 |
| | | | 705/2 |
| 2017/0071671 A1* | 3/2017 | Neumann | G16H 50/20 |
| 2017/0277841 A1* | 9/2017 | Shankar | G16Z 99/00 |
| 2018/0330800 A1 | 11/2018 | Bogue et al. | |
| 2019/0147128 A1* | 5/2019 | O'Connor | G16H 20/40 |
| | | | 703/11 |

OTHER PUBLICATIONS

Twiggs Joshua et al., "Measurement of Physical Activity in the pre- and Early Post-operative Period After Total Knee Arthroplasty for Osteoarthritis Using a Fitbit Flex Device", Medical Engineering & Physics, vol. 51, pp. 31-40, XP085319601 (Nov. 6, 2017).

Bini Stefano A et al., "Machine Learning Algorithms Can Use Wearable Sensor Data to Accurately Preduct Six-Week Patient-Reported Outcome Scores Following Joint Replacement in a Prospective Trial", The Journal of Arthroplasty, Churchill Livingstone, Amsterdam, NL, vol. 34, No. 10, pp. 2242-2247 XP085833589 (Jul. 24, 2019).

Ceaser, "The Estimation of Caloric Expenditure Using Three Triaxial Accelerometers", Doctoral Dissertation, TRACE: Tennessee Research and Creative Exchange—98 pages (Dec. 2012).

Chen et al., "Improving energy expenditure estimation by using a triaxial accelerometer", Journal of Applied Physiology, vol. 83, No. 6—11 pages (Dec. 1997.

Pande et al., "Using Smartphone Sensors for Improving Energy Expenditure Estimation", IEEE Journal of Transactional Engineering in Health and Medicine—12 pages (Sep. 18, 2015).

\* cited by examiner

SYSTEM AND METHOD FOR ASSESSING PHYSICAL ACTIVITY LEVEL USING HEALTH DATA FROM USER COMPUTING DEVICES

INCORPORATION BY REFERENCE TO ANY PRIORITY APPLICATIONS

This application claims priority to U.S. Provisional Application No. 63/036,299, filed on Jun. 8, 2020, the disclosure of which is incorporated herein by reference in its entirety for all purposes. Any and all applications for which a foreign or domestic priority claim is identified in the Application Data Sheet as filed with the present application are hereby incorporated herein by reference in their entirety under 37 CFR 1.57 for all purposes.

TECHNICAL FIELD

This disclosure relates to the field of facilitating generation, transmission, and presentation of analytics data across computing devices within in a network environment.

BACKGROUND

Patient reported outcome measures (PROM's) are often used to assess the health status of a surgical patient. For example, a PROM survey may include a number of specific questions for the patient to answer before and after the surgery. The answers to these questions may then be used to determine a numeric score, by which relative benefit can then be determined. However, these answers are inherently subjective and often measured in large chunks (e.g., weeks if not months or years), accurately predicting the efficacy of the surgery or the patient recovery pattern solely based on these answers may be difficult. Thus, more effective, granular, and objective techniques for determining the efficacy of medical interventions and predicted pattern of post-intervention recovery are desired.

DETAILED DESCRIPTION

Introduction

Figure 1:
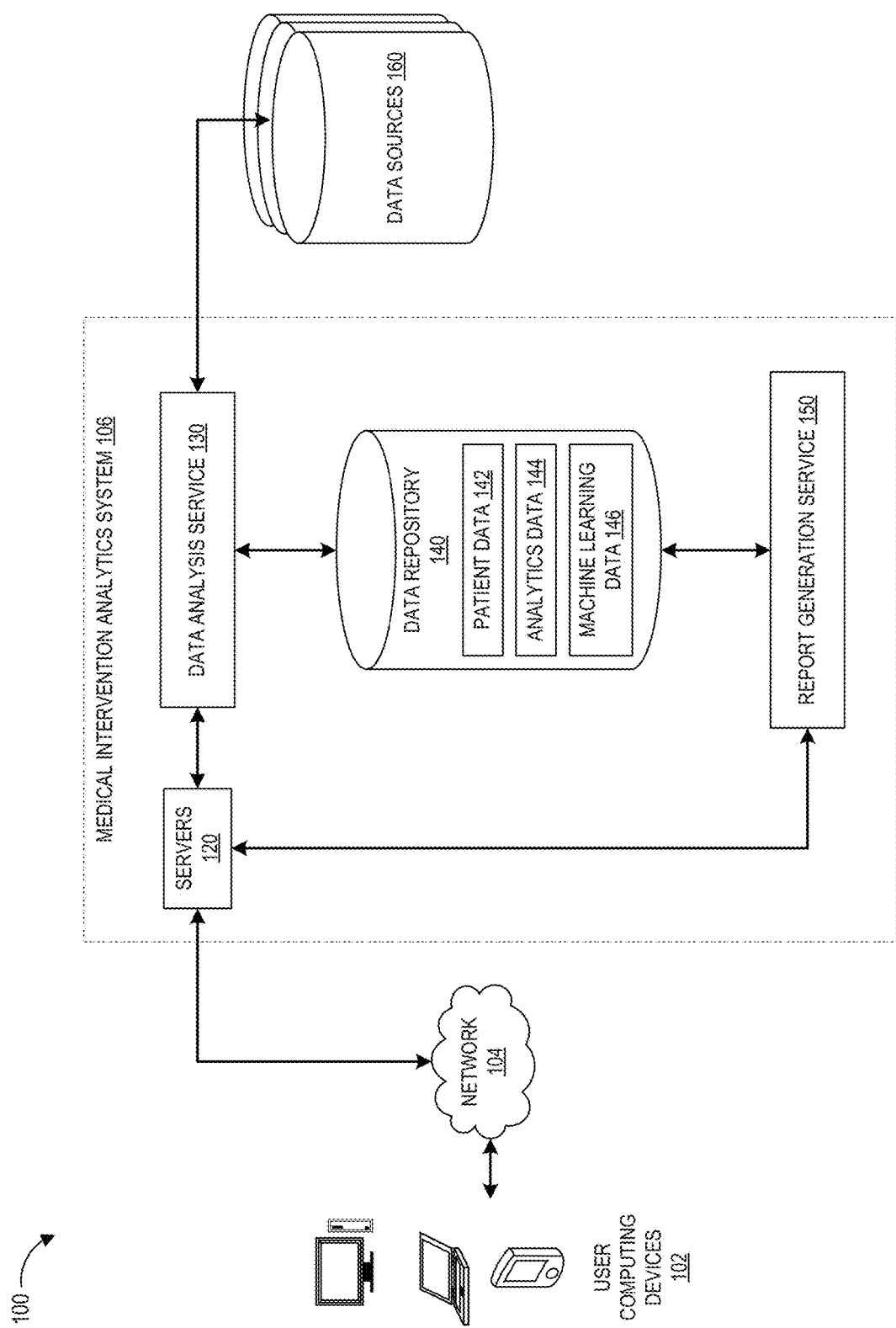
FIG. 1 depicts a schematic diagram of a network environment in which a medical intervention analytics system is used to implement a data analysis service and a report generation service in accordance with aspects of the present disclosure.

Surgeons are faced with the challenge of determining the optimal surgery for a given pathology on a daily basis. This is perhaps exemplified by spinal surgery as an example. As spinal surgery has evolved, the surgeon has access to a wide array of treatment options. Surgical decision-making, therefore, becomes an increasingly complex process, where a surgeon must parse the existing literature with each patient's unique pre-existing pathology, age, functional status and lifestyle. The complexity of this decision is reflected in studies which demonstrate 7-fold differences in the rates of lumbar laminectomies and 10-fold differences in the rate of lumbar fusions between surgical practice patterns. Perhaps even more importantly, the surgeon must decide which scientific evidence and literature to use for guidance. This is not to say that a surgeon needs to choose between a randomized controlled trial vs. a case report to determine optimal surgical approach—the hierarchy of evidence-based medicine is quite clear. Rather, the surgeon may decide how to use the existing literature to best gauge benefit vs. risks for each individual patient's overall clinical picture. This lack of clinical certainty arises in part from the fact that many pathologies of the spine have several different documented approaches—each of which is being reported as successful in one or more dimensions.

There is a large body of research regarding fusion and failure rates along with adequacy of decompression for various surgical procedures. In many cases, this type of research is driven by radiologic findings which help the surgeon to understand how the human body and bone will react to various approaches. There is likewise a large quantity of literature exploring the biomechanical advantages and disadvantages of various surgical procedures. This body of literature relies largely upon cadaveric or finite element analysis. However, surgeons realize that the patient's clinical response is perhaps the most important factor to consider. Indeed, even if the literature demonstrates the biomechanical and structural improvements after a given surgery, these findings lack relevance if they do not result in a real and meaningful improvement in the patient's quality of life.

These same issues arise in surgical decision-making in nearly every sub-specialty, including cardiac, orthopedic, bariatric, and oncologic surgery, to name a few. While the technical aspects of the sub-specialties differ, in all surgical fields the physician struggles to apply relevant outcomes-driven research to modify practice patterns at the individual patient and population levels.

To date, measuring the success of the surgery has relied on Patient Reported Outcome Measures (PROM's). The vast majority of PROM's are surveys which ask the patient to answer a number of specific questions before and after the surgery. The answers to these questions are then used to determine a numeric score, by which relative benefit can then be determined. There are a number of different PROM surveys in existence, and for spine the most commonly utilized include the Oswestry Disability Index (ODI), visual analog scale (VAS) back pain and leg pain, and the Neck Disability Index (NDI), just to name a few. More general PROM's can be applied across multiple arenas of human function, such as the Short Form (SF)-36 health survey.

While these PROM surveys do represent an important conceptual leap forward, there are a number of problems with relying solely upon them to gauge benefit. First is their inherently subjective nature. The fact that a patient feels or states that they are more functional does not necessarily mean that it is so. These surveys are undoubtedly subject to a number of biases which the patients consciously or unconsciously incorporate into their responses.

Additionally, there seems to be a broad lack of standardization in terms of which PROM to use. A retrospective review of orthopedic spine journals noted 206 different PROM's used across 1,079 studies. Perhaps equally as importantly, there was a notable lack of consistency in terms of methodology and score calculation even amongst the most commonly used PROM's. This highlights yet another issue with PROM's—namely, that if these metrics are not standardized or consistently calculated, their utility in demonstrating relative value and treatment efficacy is limited. How should we standardize them? Which metrics are most effective? And over what time-frame should they be used to predict outcomes? One notable study found that 3 month PROM data did not reliably predict 12 month outcomes on an individual patient level. Should the surgeon then continue to collect PROM data for 1 year? Perhaps 2 years? The answers to these questions remain murky at best.

With the advent of modern technology, we now have the means to accurately capture daily activity on both a retrospective and prospective basis. For example, a user's smartphone may be equipped with numerous sensors (e.g., accelerometer, gyroscope, compass, etc.) that can generate sensor data, and the smartphone may, with the help of one or more mobile applications installed thereon, calculate or estimate various indicators of user mobility such as step count, step size, distance traveled, flights of stairs climbed, calorie count, standing minutes, active minutes, etc. This activity data will be free of user bias, and will provide a true measure of functional status. By processing and analyzing the activity data that has already been captured and stored by multitude of personal mobile devices (e.g., smartphones, smartwatches, fitness trackers, etc.), the techniques of the present disclosure can apply a consistent and objective computer algorithm, provide an excellent tool for measuring human function. By analyzing these activity of patients, the present disclosure provides an objective method of measuring pre-op and post-op functional statuses of the patients.

For example, utilizing existing health data stored on smartphones, it is possible to capture information on thousands of patients who have already undergone surgeries retrospectively. By capturing a much larger number of patients, the results are powered to detect objective improvement or worsening of patient's or population's functional status after undergoing surgery. This analyzed data and metric will be valuable in helping to gauge not only the impact of various types of medical interventions, but also the timing of this impact, and its relationship to patient baseline characteristics. This objective measurement of surgical intervention can be the key to developing value-based reimbursement model for Medicare/Medicaid/private insurance companies. Under the current fee-for-service model, the reimbursements are based not on the patient outcome but rather on the types of procedures (CPT) and the diagnosis codes (ICD-10). Objective, reliable, consistent and accurate objective real-time activity levels of pre- and post-surgical patients will allow this paradigm shift in the business of medical care in the United States.

The present disclosure includes a method of safely, securely, and efficiently collecting large quantities of post-processed activity data collected and stored within user computing devices such as smartphones. For instance, a smartphone may have a built-in three-axis accelerometer as well as three-axis gyroscope, which are usable to calculate and track the number of steps based on speed and movement of the smartphone. By combining demographics data such as age, gender, height and weight of the user, the triaxial accelerometer can be used to estimate energy expenditures during physical activities by the pre-defined empirical relationship between accelerometer and energy expenditure data measured by a calorimeter. While this data is potentially useful to the typical consumer, it remains only loosely relevant from the perspective of monitoring health status. In its current form, the data that is presented appears largely to be of interest to those involved in general fitness or athletic endeavors, and thus falls short of being useable as a health metric or outcome measure. A raw number of steps before and after the date of surgery will be meaningless unless those numbers are compared to a large cohort of patients who underwent similar surgery. For instance, if Ms. Jones underwent one-level lumbar microdiscectomy and her pre-operative steps per day went from 4000 to 6000 at one-year post-op, what does that mean? Should she be at 8000 steps per day at one-year post-op to qualify her activity level as "good" outcome? How do you define baseline pre-op steps per day? How do you make these activity levels clinically meaningful?

The aforementioned challenges and questions, among others, are addressed in some embodiments by the disclosed techniques for processing patient data, determining a predicted surgical efficacy (e.g., how the physical conditions such as the mobility of the patient might improve) of a proposed surgical intervention (e.g., spine surgery), and determining a predicted pattern of post-operative recovery (e.g., the number of steps that the patient can expect to take 15 days, 30 days, or 90 days from the surgery date) for the patient, among others, are described herein. More specifically, the present disclosure provides a system that can analyze the patient data of a plurality of patients data, generate analytics data indicating the post-operative recovery of the plurality of patients, and store the analytics data in association with the biological traits of the patients and the types of surgical interventions that the patients underwent. Subsequently, the system can analyze the patient traits and activity data of a new patient, and output, based on the previously generated analytics data, a prediction of how efficacious a given surgical intervention might be for that patient and/or how the patient might recover from the given surgical intervention.

As will be appreciated by one of skill in the art in light of the present disclosure, the embodiments disclosed herein improve the ability of computing systems, such as data analysis systems, data processing systems, machine learning systems, etc., to provide more efficient and effective data analysis techniques. By utilizing the pre-op and post-op health data or sensor data generated based on the movement of user computing devices, generating visual comparisons and predictions, and utilizing and updating machine learning algorithms usable to generate such visual comparisons and predictions, the medical intervention analytics system of the present disclosure can address the deficiencies described above.

These and other aspects of the disclosure will now be described with regard to certain examples and embodiments, which are intended to illustrate but not limit the disclosure. Although the examples and embodiments described herein will focus, for the purpose of illustration, on specific calculations and algorithms, one of skill in the art will appreciate the examples are illustrate only, and are not intended to be limiting.

Technical Advantages

Temporally granular data—Traditional metrics are typically assessed at predetermined time points. This is not only onerous, but also misses data between the sampling times. Existing PROM's are sampled with gaps in the range of weeks, to months, to years. The techniques described herein (also referred to herein as Objective Realtime BioInformation Tracker, "ORBIT" in some embodiments) allow the user to sample potentially any specific time point for comparison, and also allows the analysis to be from aggregated time points to further overcome sampling errors. This ability to continuously monitor the progress is critical since it can allow for early detection of either improvement or worsening before the patient comes back to the clinic. PROM is only collected when the patient fills out a survey, whereas the techniques for analyzing the patient data described herein can be applied on a real-time basis and updated as soon as the physical activity data is imported from the patient's smartphones (e.g., all activity data can be imported initially, and additional activity data can be imported periodically (e.g., every 2 weeks) or on demand (e.g., whenever the user wishes to generate or visualize updated analytics data, which may be indicated by the user activating a user interface element presented on the user computing device 102)).

Automatic collection—The techniques described herein may not need to rely on any specific patient or provider action as data can be collected passively. This may overcome patient compliance issues and also avoid the possibility of inadvertently missing the opportunity to sample data.

Prospective data analytics—The software application allows for efficient prospective data collection and analysis. For the patient as a user this could represent a real-time feedback mechanism by which to modify and improve behavior. For instance, if there is a decline in ORBIT, this would trigger an alert to the patient and the treating physician, and they can decide whether a clinic visit is needed. For the analyst this allows for early detection of any variances which could provide useful indicators of patient performance after an intervention.

Retrospective data analytics—Using a methodology analogous to the prospective data collection and analysis, data can also be retrieved retrospectively. This is a powerful tool leveraging the smartphone and any associated cloud-based data storage systems in use. Data abstracted going back years for any given individual or patient can be analyzed in aggregate. For example, one of the differentiating elements of the data analysis techniques described herein is the ability for the user to abstract a meaningful health outcome metric from previously stored data. Unlike PROM, which requires a patient to fill out a survey in order to come up with the score, ORBIT can be calculated based on physical activity data from the date of purchase of a smartphone. Most users will have interest in evaluating a health outcome measure at time points before intent or action was undertaken. This is particularly valuable in health outcomes research, efficacy studies of interventions, and evaluation of a previous health events in a patient's life. ORBIT allows determination of a baseline and any follow-up time point in the past to be objectively measured. This allows the user of the software application to ascertain objectively the health metric at potentially any previous time point that the user has had smartphone technology. Thus, users who have already undergone previous interventions can be studied in a granular and objective manner. This presents a utility to the patient as well as stakeholders in any medical intervention as nearly all previous health metrics required prospective collection of a baseline metric at a minimum or some element of non-standardized data interpolation.

Machine-based learning—Existing PROM's remain fixed in their manner of data query. Because of the elemental nature as well as size of the datasets collected and analyzed, ORBIT can leverage machine-based learning to adapt and increase its relevance as a health measure. Machine learning algorithms may be generated and continually trained using relevant independent variable to predict pre- and post-surgical activity level.

Analysis across non-linear dynamic ranges of measurement—The numerical simplicity of existing PROM's are appealing but improbably reflect the true nature of a biological system. ORBIT allows non-linear measurement of patient performance. While the datasets are composed of linear measurements, the ability to post-process data allows for the ORBIT metric to detect and convey health information in the most important dynamic ranges. In particular, sensitivity to changes at the low end of human performance are most likely to carry the greatest medical relevance.

These and other aspects of the disclosure will now be described with regard to certain examples and embodiments, which are intended to illustrate but not limit the disclosure. Although the examples and embodiments described herein will focus, for the purpose of illustration, on specific calculations and algorithms, one of skill in the art will appreciate the examples are illustrate only, and are not intended to be limiting.

Overview of Example Computing Environment for Medical Intervention Analytics System The illustrative network environment 100 shown in FIG. 1 includes a medical intervention analytics system 106 according to one embodiment. The medical intervention analytics system 106 enables a user (e.g., a patient, a medical professional, a researcher, a data scientist, a medical intervention evaluator, etc.) to utilize the data analysis service and the report generation service provided via the medical intervention analytics system 106. The user may input patient data (e.g., age, gender, ethnicity, height, weight, co-morbidities, etc.) and/or answer a set of questions via a user interface presented on the user computing device 102, along with information relating to the surgery that has already been performed or to be performed (e.g., surgery date, surgery type, etc.), which may be transmitted to the medical intervention analytics system 106 (or to a data repository accessible by the medical intervention analytics system 106). In response, the medical intervention analytics system 106 may output a report based on the provided information. The details of the data analysis and the report generation are described in greater detail below.

By way of illustration, various example user computing devices 102 are shown in communication with the medical intervention analytics system 106 via network 104. The user computing devices 102 can be any computing device such as a desktop, a laptop, a mobile phone (or smartphone), a tablet, a kiosk, a television, a wristwatch (including a smartwatch), a fitness tracker, a wireless device, a media player, one or more processor devices, integrated circuit components for inclusion in computing devices, and the like.

The network 104 over which the user computing devices 102 can access the medical intervention analytics system 106 may be any wired network, wireless network, or combination thereof. In addition, the network 104 may be a personal area network, local area network, wide area network, over-the-air broadcast network (for radio or television, for example), cable network, satellite network, cellular telephone network, or combination thereof. For example, the network 104 may be a publicly accessible network of linked networks, possibly operated by various distinct parties, such as the Internet. In some embodiments, the network 104 may be a private or semi-private network, such as a corporate or university intranet. The network 104 may include one or more wireless networks, such as a Global System for Mobile Communications (GSM) network, a Code Division Multiple Access (CDMA) network, a Long Term Evolution (LTE) network, or any other type of wireless network. The network 104 can use protocols and components for communicating via the Internet or any of the other aforementioned types of networks.

In the depicted embodiment, the medical intervention analytics system 106 includes servers 120, which can communicate with the user computing devices 102 over the network 104 and provide access to various services of the medical intervention analytics system 106. In the example of FIG. 1, the services provided by the medical intervention analytics system 106 include a data analysis service 130 and a report generation service 150. In some embodiments, these services can be implemented as software components executing in physical computer hardware on the servers 120 or in separate computing devices. The term "service," as used herein and in addition to its ordinary meaning, may in some embodiments also refer to the underlying physical hardware implementing the operations described herein.

The medical intervention analytics system 106 may provide user interfaces (and/or instructions therefor) for display upon the user computing devices 102, for example, via a navigation and/or browsing interface such as a browser or application installed on the user computing devices 102, and the users on the user computing devices 102 may utilize the various services provided by the medical intervention analytics system 106 such as the data analysis service 130 and the report generation service 150 via the user interfaces.

The data analysis service 130 can access data repository 140 and/or data sources 160 to collect and/or generate certain patient data, analytics data, machine learning data, or any portions thereof to perform the data analyses described herein. The report generation service 150 can access the analytics data from the data repository 140 and generate reports and/or user interfaces to convey various visual indicators, predictions, and results of the patient and medical intervention analytics described herein.

In some embodiments, data generated by the user computing devices 102 may be sent directly to the system 106 (e.g., and stored in the data repository 140) or to the data sources 160 (e.g., by the mobile application installed on the user computing devices 102) for retrieval by the data analysis service 130 (for use in the analytics performed by the data analysis service 130 and/or for subsequent storing in the data repository 140). Although the data sources 160 are shown outside the medical intervention analytics system 106, in some embodiments, some or all of the data sources 160 may be implemented within the medical intervention analytics system 106.

The data repository 140 may store patient data 142, analytics data 144, and machine learning data 146. The patient data 142 may include biological and other traits associated with patients (e.g., age, gender, ethnicity, height, weight, co-morbidities, etc.), activity data associated with patients (e.g., raw activity or sensor data and/or processed activity data such as step count, step size, number of flights climbed, distance traveled, calorie count, standing minutes, active minutes, gait asymmetry, etc.), and surgery data associated with patients (e.g., details relating to a medical intervention that a patient has undergone or will be undergoing, such as medical practitioner, medical intervention date, medical device used, medical device manufacturer, medical intervention duration, level of invasiveness, medical intervention time of day, etc.). In some embodiments, the patient data 142 may be provided by multiple users (e.g., by a user computing device 102 of the patient as well as a user computing device 102 of the physician/evaluator/researcher/etc.) and cross-checked and/or de-duplicated.

The analytics data 144 may include, for example, (i) processed versions of the patient data such as averages, sums, aggregates, subsets, z-scores, means, standard deviations, graphs, charts, etc., (ii) data points of interest such as acute decline, post-op recovery, etc., and (iii) temporal windows (also referred to herein as epochs) identified using the patient data 142 and/or other analytics data, (iv) medical intervention efficacy scores described herein, (v) patient improvement indices (e.g., how this particular patient is doing pre-op and/or post-op compared to other similarly situated patients, based on the patient data), (v) predictions of medical intervention efficacy scores and/or recovery patterns (e.g., graphs, tables, or other indicators of how a patient might recover), to name a few examples.

The machine learning data 146 may include one or more machine learning models or algorithms generated and/or trained by the medical intervention analytics system 106. One or more of these prediction models may be used to determine an expected value or occurrence based on a set of inputs. For example, a prediction model can be used to predict a patient's future activity levels based on one or more inputs to the prediction model, such as, for example, patient data described herein, medical intervention data, past activity data of the patient, and previously analyzed patient data, medical intervention data, and activity data of other users. A number of different types of algorithms may be used by the medical intervention analytics system 106. For example, certain embodiments herein may use a logistical regression algorithm. However, other algorithms are possible, such as a linear regression algorithm, a discrete choice algorithm, or a generalized linear algorithm.

The medical intervention analytics system 106 is depicted in FIG. 1 as operating in a distributed computing environment including several computer systems that are interconnected using one or more computer networks. The medical intervention analytics system 106 could also operate within a computing environment having a fewer or greater number of devices than are illustrated in FIG. 1. Thus, the depiction of medical intervention analytics system 106 in FIG. 1 should be taken as illustrative and not limiting to the present disclosure. For example, the medical intervention analytics system 106 or various constituents thereof could implement various Web services components, hosted or "cloud" computing environments, and/or peer-to-peer network configurations to implement at least a portion of the processes described herein.

Further, the medical intervention analytics system 106 and its components may be implemented in hardware and/or software and may, for example, include one or more physical or virtual servers implemented on physical computer hardware configured to execute computer executable instructions for implementing the various features described herein. The one or more servers may be geographically dispersed or geographically co-located, for example, in one or more data centers. In some embodiments, one or more of the components shown in FIG. 1 may be implemented on one or more virtual servers or virtual machines.

Moreover, the processing of the various components or services of the medical intervention analytics system 106 can be distributed across multiple machines, networks, or other computing resources. The various components or services of the medical intervention analytics system 106 can also be implemented in one or more virtual machines or hosted computing environment (for example, "cloud") resources, rather than in dedicated servers. Likewise, the data repositories shown can represent local and/or remote, physical and/or logical data storage, including, for example, storage area networks or other distributed storage systems. In some embodiments, the connections between the components or services shown represent possible paths of data flow, rather than actual connections between hardware. Executable code modules that implement various functionalities of the medical intervention analytics system 106 can be stored in the memories of the servers 120 and/or on other types of non-transitory computer-readable storage media. While some examples of possible connections are shown, any subset of the components shown can communicate with any other subset of components in various implementations.

Processing Patient Activity Data

Figure 2:
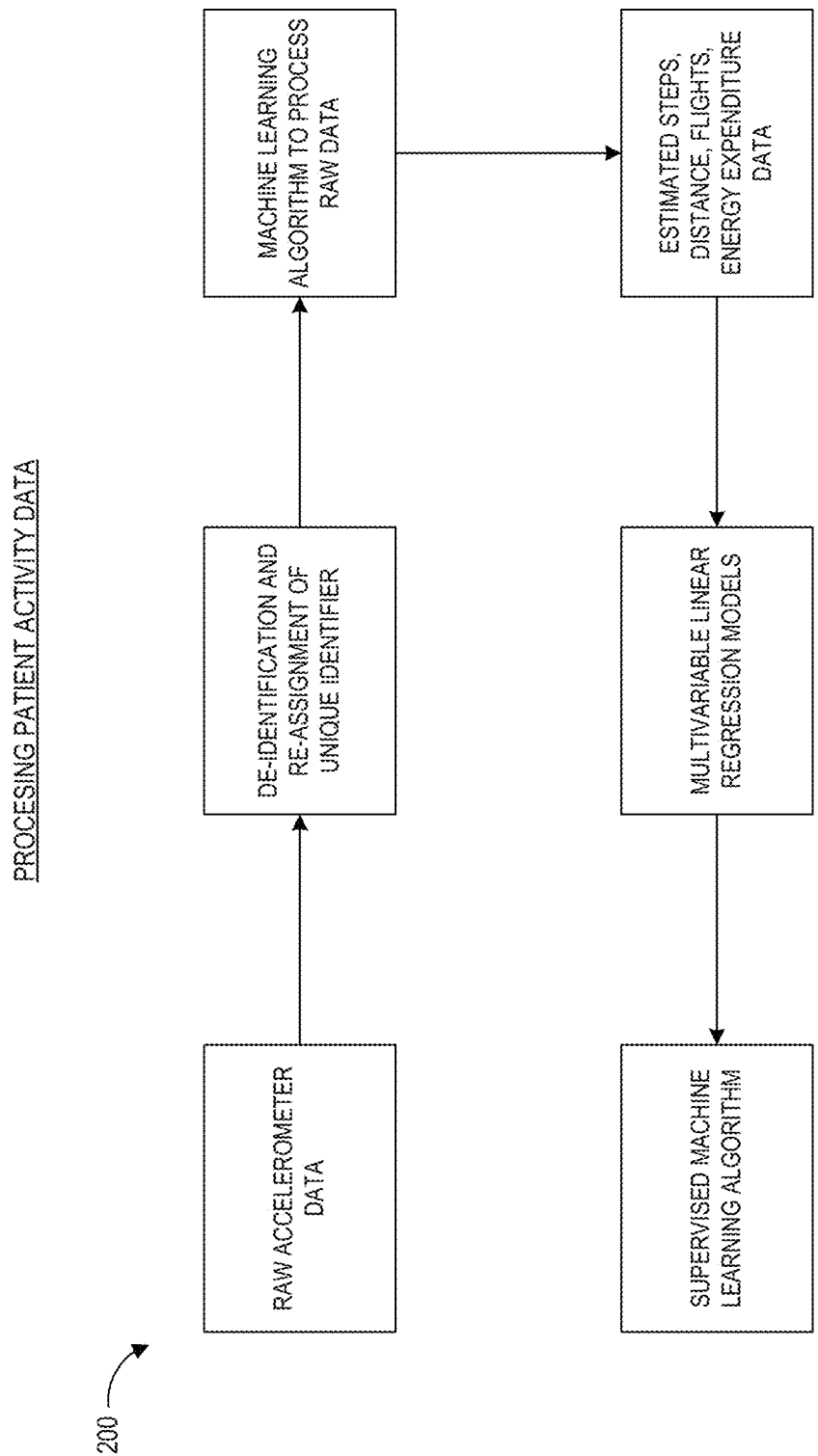
FIG. 2 depicts a block diagram illustrating an example work flow of processing patient activity data, in accordance with aspects of the present disclosure.

FIG. 2 depicts an illustrative data flow 200 for processing patient activity data in accordance with aspects of the present disclosure. As shown in FIG. 2, the data flow 200 may include (i) raw accelerometer data, (ii) de-identified and re-assigned unique identifiers, (iii) machine learning algorithms, (iv) estimated steps, distances, flights, and energy expenditure data, (v) multivariable linear regression models, and (vi) supervised machine learning algorithms. For example, the system 106 may have the capacity to automatically deidentify the user's personal information and assign a unique identifier to the imported dataset. Once the user has consented to the data sharing agreement, the mobile application installed on the user's computing device may continually extract and populate the database on the cloud on-going basis. Raw accelerometer data may then be processed to calculate physical activity parameters such as steps taken, distance travelled, flights climbed, standing minutes, and energy expenditure using an existing algorithm. Once physical function data has been generated for an individual user, these data points may be added to the library of database that contains previously collected data.

Once the steps, distance, flights, calorie, and standing minute data has been generated for each patient, these data are organized into daily, weekly, and monthly averages. For each parameter (e.g., average steps per day, distance per day, active calorie burned, flights climbed and standing minute), outliers (e.g., more than 2 standard deviations away from the mean) may be removed, and a graph may be generated. Once the parameters are collected for each patient, these are displayed in a dashboard format where the time to achieve or exceed the baseline activity level are displayed. In addition, the graphs are generated for each parameter as well.

Using the described steps below, an ORBIT score may be calculated for each patient. Multivariable linear regression may be used to generate a model based on the existing independent variables such as age, sex, ethnicity, baseline medical co-morbidities, type of surgery, level of surgery, pre-operative baseline physical activity, post-operative physical activity levels and others. Multivariable linear regression model will be updated daily. Supervised learning for machine learning algorithm may be performed by inputting independent variables (age, gender, body mass index, surgery type, baseline physical function, etc.) to predict a user's physical function after surgery (e.g., steps, distance, energy expenditure, flight climbed and standing time).

In some embodiments, based on five physical function metrics (steps per day, distance per day, active calorie burned, flights climbed and standing minute), an ORBIT (Objective Realtime BioInformation Tracker) score can be calculated for each subject. This is a composite scoring method that will be validated against PROM. Pearson correlation coefficients will be calculated between PROMs and ORBIT to see if there is divergence or correlation between the two. Each components of the ORBIT will be given a weighted score. This data will be invaluable in helping to gauge not only the impact of various types of surgical interventions, but also the timing of this impact, and its relationship to patient baseline characteristics. ORBIT takes into account of time to recovery and the amount of recovery; therefore, its score reflects how fast or slow the patient recovered and how much each physical activity parameters (steps, distance, calorie, flights climbed and standing minutes) changed after surgery. ORBIT score is calculated using existing patient's physical data and its details are described below. ORBIT can also be predicted using machine learning algorithm for individual patients who has not yet gone through a surgery based on their baseline characteristics and their pre-operative physical activity level data.

An example of calculating the ORBIT score is described below:

Keywords:
Steps per day=SPD
Distance per day=DPD
Active Calorie Burned=ACB
Stand Minutes=SM Flights Climbed=FC
ODI=Oswestry Disability Index
NDI=Neck Disability Index The ORBIT score is a weighted scoring system for SPD, DPD, ACB, SM, FC and present a combined scoring to reflect:

Time to return to baseline SPD, DPD, ACB, SM, FC
Grade SPD, DPD, ACB, SM, FC

The ORBIT score is a composite weighted score, taking into account changes in 5 domains of physical activity from their baseline to the time of assessment. There is two dimensions, temporal and gradient, to 5 main domains of physical activity measures. The ORBIT score can range from −15 to 25, higher score representing more physical activity, lower scores representing less physical activity.

Steps per day (SPD):
Mean baseline steps per day (1YbSPD),(9MbSPD), (6MbSPD),(3MbSPD) is defined by the total number of steps 1 year, 9 months, 6 months, and 3 months prior to the surgery and up to a day before the surgery divided by 365 days.
  bSPD=total number of steps over 1 year period/365 days
  Day of surgery will be the day 0
SPD will be reported in mean and standard deviation included for all patients
SPD will be organized in weekly manner
  W0=the week of surgery, day 0-6 then W1, W2, W3 . . . etc
  Weekly SPD
    W0SPD=(total number of steps in week 0)/7 days
  bSPD (365 days), W0SPD, W1SPD, W2SPD, W3SPD, W4SPD, W5SPD, W0SPD, W12SPD, M6SPD, M9SPD, Y1SPD, Y2SPD
Time to achieve bSPD (Temporal Component)
  Early Recovery (ER): those who achieved or exceeded pre-op bSPD within W12
  Late Recovery (LR): those who achieved or exceeded pre-op bSPD from W13 to Y2
  No Recovery (NR): those who never achieved or exceeded pre-op bSPD from W0 to Y2
Grading the achievement from M6 to Y2
  M6-Y2 SPD will be defined by the total steps from M6 to Y2/540 days
    Severe Worsening (SW): those who are 0% to 49% of bSPD
    Moderate Worsening (MoW): those who are 50% to 75% of bSPD
    Mild Worsening (MW): those who are 76% to 99% of bSPD
    Mild Recovery (MR): those who are 100% to 125% of bSPD
    Moderate Recovery (MoR): those who are 126% to 150% of bSPD
    Significant Recovery (SR): those who are 151% to 200% of bSPD Distance per day (DPD)—This is another indicator of mobility in addition to the steps per day.
  bDPD=total distance travelled over 1 year period/365 days
  DPD will be organized in weekly manner
  Time to achieve DPD and beyond
    Early Recovery (ER): those who achieved or exceeded pre-op bDPD within W12
    Late Recovery (LR): those who achieved or exceeded pre-op bDPD from W13 to Y2
    No Recovery (NR): those who never achieved or exceeded pre-op bDPD from W0 to Y2
    Deterioration (D): those who experience worsening in pre-op bDPD by Y2
  Grading the achievement from M6 to Y2
    M6-Y2 DPD will be defined by mean DPD from M6 to Y2/540 days
      Severe Worsening (SW): those who are 0% to 49% of bDPD
      Moderate Worsening (MoW): those who are 50% to 75% of bDPD
      Mild Worsening (MW): those who are 76% to 99% of bDPD
      Mild Recovery (MR): those who are 100% to 125% of bDPD
      Moderate Recovery (MoR): those who are 126% to 150% of bDPD
      Significant Recovery (SR): those who are 151% to 200% of bDPD Active Calorie Burned (ACB)—This would be a powerful indication of activity level for the patients that may not be reflected necessarily in the SPD. Similar ways to capture and report the data as SPD.
  Mean baseline active calorie (kCal) burned (bACB) is defined by the total active calorie burned over 1 year prior to the surgery and up to a day before the surgery divided by 365 days.
    bACB=total ACB (kCal) over 1 year period/365 days
    Day of surgery will be the day 0
  ACB will be reported In mean and standard deviation included for all patients
  ACB will be organized in weekly manner as above
    W0=the week of surgery, day 0-6 then W1, W2, W3 . . . etc
  Time to achieve
    Early Recovery (ER): those who achieved or exceeded bACB within W12
    Late Recovery (LR): those who achieved or exceeded bACB from W13 to Y2
    No Recovery (NR): those who never achieved or exceeded bACB from W0 to Y2
  Grading the achievement from M6 to Y2
    M6-Y2 ACB will be defined by the total ACB from M6 to Y2/540 days
      Severe Worsening (SW): those who are 0% to 49% of bACB
      Moderate Worsening (MoW): those who are 50% to 75% of bACB
      Mild Worsening (MW): those who are 76% to 99% of bACB
      Mild Recovery (MR): those who are 100% to 125% of bACB
      Moderate Recovery (MoR): those who are 126% to 150% of bACB
      Significant Recover (SR): those who are 151% to 200% of bACB Stand Minutes (SM):
bSM=total stand minute over 1 year period/365 days
SM will be organized in weekly manner
Time to achieve bSM and beyond
  Early Recovery (ER): those who achieved or exceeded pre-op bSM within W12
  Late Recovery (LR): those who achieved or exceeded pre-op bSM from W13 to Y2
  No Recovery (NR): those who never achieved or exceeded pre-op bSM from W0 to Y2
Grading the achievement from M6 to Y2

M6-Y2 SM will be defined by mean SM from M6 to Y2/540 days
- Severe Worsening (SW): those who are 0% to 49% of bSM
- Moderate Worsening (MoW): those who are 50% to 75% of bSM
- Mild Worsening (MW): those who are 76% to 99% of bSM
- Mild Recovery (MR): those who are 100% to 125% of bSM
- Moderate Recovery (MoR): those who are 126% to 150% of bSM
- Significant Recovery (SR): those who are 151% to 200% of bSM Flights Climbed (FC):
bFC=total flights climbed over 1 year period/365 days
FC will be organized in weekly manner
Time to achieve bFC and beyond
- Early Recovery (ER): those who achieved or exceeded pre-op bFC within W12
- Late Recovery (LR): those who achieved or exceeded pre-op bFC from W13 to Y2
- No Recovery (NR): those who never achieved or exceeded pre-op bFC from W0 to Y2
- Deterioration (D): those who experience worsening in pre-op bFC by Y2

Grading the achievement from M6 to Y2
M6-Y2 FC will be defined by mean SM from M6 to Y2/540 days
- Severe Worsening (SW): those who are 0% to 49% of bFC
- Moderate Worsening (MoW): those who are 50% to 75% of bFC
- Mild Worsening (MW): those who are 76% to 99% of bFC
- Mild Recovery (MR): those who are 100% to 125% of bFC
- Moderate Recovery (MoR): those who are 126% to 150% of bFC
- Significant Recovery (SR): those who are 151% to 200% of bFC

TABLE 1

Example Grading Scheme

|  | Time to achieve or exceed baseline (0 to 2) | Grading Achievements (−3 to 3) | Composite Score |
|---|---|---|---|
| SPD |  |  |  |
| DPD |  |  |  |
| ACB |  |  |  |
| SM |  |  |  |
| FC |  |  |  |
| Total Score |  |  |  |

Multivariate analysis and identify factors which contribute to (Odds Ratio)
Surgical factors:
- Cervical surgery
- Lumbar surgery
- Fusion vs. non-fusion
- Number of levels Demographics:
- BMI
- Age
- Sex
- Average preoperative activity level Oswestry Disability Index for Lumbar Spine Surgery
Neck Disability Index for Cervical Spine Surgery
These outcomes will be compared to baseline and Y2 NDI for cervical and Y2 ODI for lumbar surgeries:
NDI
- Good outcome will be 0-28
- Bad outcome will be 15-50

ODI
- Good outcome 0-20
- Bad outcome 21-100

Pearson correlation coefficients were calculated between NDI/ODI and ORBIT to check divergence.

Example of Patient Experience

An example patient experience is described below. Health metrics (steps taken, distance travelled, flights climbed, standing minutes and energy expenditure, etc.), patient traits (age, sex, ethnicity, co-morbidities, etc.), and surgery details (type of surgery, levels of surgery, location of surgery, identity of surgeon/hospitals) are collected from 1000s of patients via the app.

a. Individual patients download the mobile app onto their smartphones
b. Mobile app determines pre-op and post-op health metrics based on the date of surgery (e.g., by extracting existing health data stored on the patient's smartphone)—the mobile app continues to collect post-op health metrics
c. Mobile app sends all data to the server The system 106 analyzes the data received from 1000s of patients and generates a model.

Ms. Jones comes in for a checkup and consents to download the mobile app and share her activity data with the treating surgeon. Once the patient opens the app and consents to share the data, the app starts to upload activity data onto the HIPAA-compliant and encrypted cloud (e.g., system 106 or data sources 160).

She downloads the mobile app:
d. Mobile app determines her pre-op health metrics
e. Mobile app determines her patient traits
f. Mobile app sends off the data to the server
g. Server performs analysis using the model, generates projections, sends to mobile app
h. Mobile app processes the data downloaded from the server, generates user interface into a dashboard displaying her activity metrics and also into graphs For patients who already underwent surgery, their pre-operative and post-operative activity level is organized and displayed into a dashboard. For those who has not undergone surgery yet, they can choose the type of surgery they are expected to undergo on a future date. The machine learning algorithm is then able to generate expected physical activity levels taking into consideration of the patient's baseline characteristics and baseline activity levels.

Type of surgery (e.g., minimally invasive or open, cervical or lumbar, 1 or 2 levels of surgery) can be entered into the database. Mobile app is also able to generate future expected activity level using machine learning algorithm if the patient has not yet undergone surgery.

Surgery is performed:
i. Mobile app collects surgery detail from the treating surgeon and the patient
j. Mobile app begins collecting post-op health data
k. Mobile app compares post-op data to previously generated projection and to baseline and updated on weekly basis i. Actual physical activity data can be compared to computer generated data and any discrepancy can be calculated and displayed in a graph and dashboard format
   ii. Any discrepancy will be continuously fed back into the machine learning algorithm to improve its accuracy and its ability to predict
  l. Trigger feedback/suggestions to the patients and to the surgeons
   i. If the patient is not meeting the expected milestones (e.g. by 6 weeks post-op, if the patient is expected to be taking 5000 steps per day, but the patient is at 4000 steps per day), the patient will receive an encourage message and a reminder to their smartphone that they are reaching their expected activity level. Not only the app will provide the feedback, it will display the patient's physical activity data in a dashboard fashion, so that the patient will be able to see their data visualized in a succinct and organized fashion. In addition, the patients will be able to see their ORBIT metric, which is a composite objective activity measure that takes account of multiple dimensions of physical activities, and also correlated with established patient reported outcome measures (PROM)s.
   ii. At the same time, the surgeon will have an option to be notified and alerted if the patient has a sharp decline in their activity level post-operatively, which may trigger a visit to the emergency room or a follow-up in clinic.

Aggregated data from thousands of patients will be fed into machine learning algorithm, which will continuously learn and improve over time. This algorithm will then be utilized to predict outcomes of other medical or surgical interventions (e.g. a new anti-depressant medication or orthopedic hip joint replacement).

Example Routine for Performing a Post-Operative Analysis of Patient Data

Figure 3:
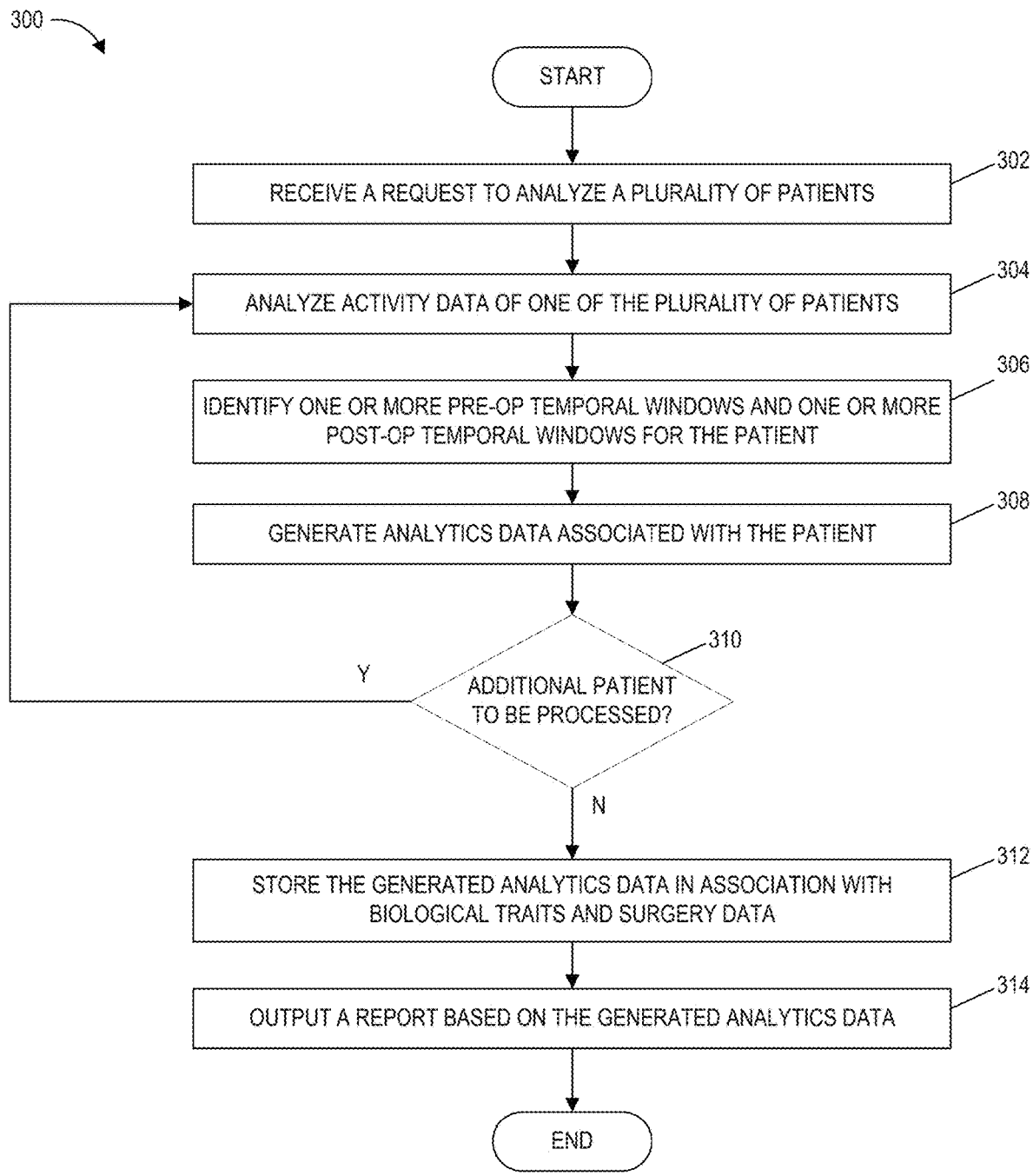
FIG. 3 is a flowchart of an example process for performing a post-op analysis of patient data, in accordance with aspects of the present disclosure.

FIG. 3 depicts an illustrative routine 300 for performing a post-operative analysis of patient data in accordance with aspects of the present disclosure. The routine 300 may be carried out, for example, by the data analysis service 130 and/or the report generation service 150 or one or more other components of the medical intervention analytics system 106 described herein. For convenience, some or all of the steps of the routine 300 are described as being performed by the system 106. For example, the system 106 may include one or more hardware computing devices and non-transitory physical computer storage storing instructions that, when executed by the one or more hardware computing devices, cause the one or more hardware computing devices to perform the steps of the routine 300.

The routine 300 begins at block 302, at which the system 106 receives a request to analyze a plurality of patients.

At block 304, the system 106 analyzes the activity data of one of the plurality of patients.

At block 306, the system 106 identifies one or more pre-op temporal windows and one or more post-op temporal windows for the patient.

At block 308, the system 106 generates analytics data associated with the patient.

At block 310, the system 106 determines whether there is any additional patient to be processed. If the system 106 determines that there exists an additional patient to be processed, the routine 300 returns to block 304. Otherwise, the routine 300 proceeds to block 312.

At block 312, the system 106 stores the analytics data generated for each patient in association with the biological traits data and the surgery data associated with the corresponding one of the plurality of patients.

At block 314, the system 106 outputs a report based on the generated analytics data. The routine 300 may then end.

The routine 300 can include fewer, more, or different blocks than those illustrated in FIG. 3 and/or one or more blocks illustrated in FIG. 3 may be modified, omitted, or switched without departing from the scope of the description. Moreover, it will be appreciated by those skilled in the art and others that some or all of the functions described in this disclosure may be embodied in software executed by one or more processors of the medical intervention analytics system 106 and/or the user computing device 102 disclosed herein.

Illustrative Graphs and User Interface Elements

Figure 4:
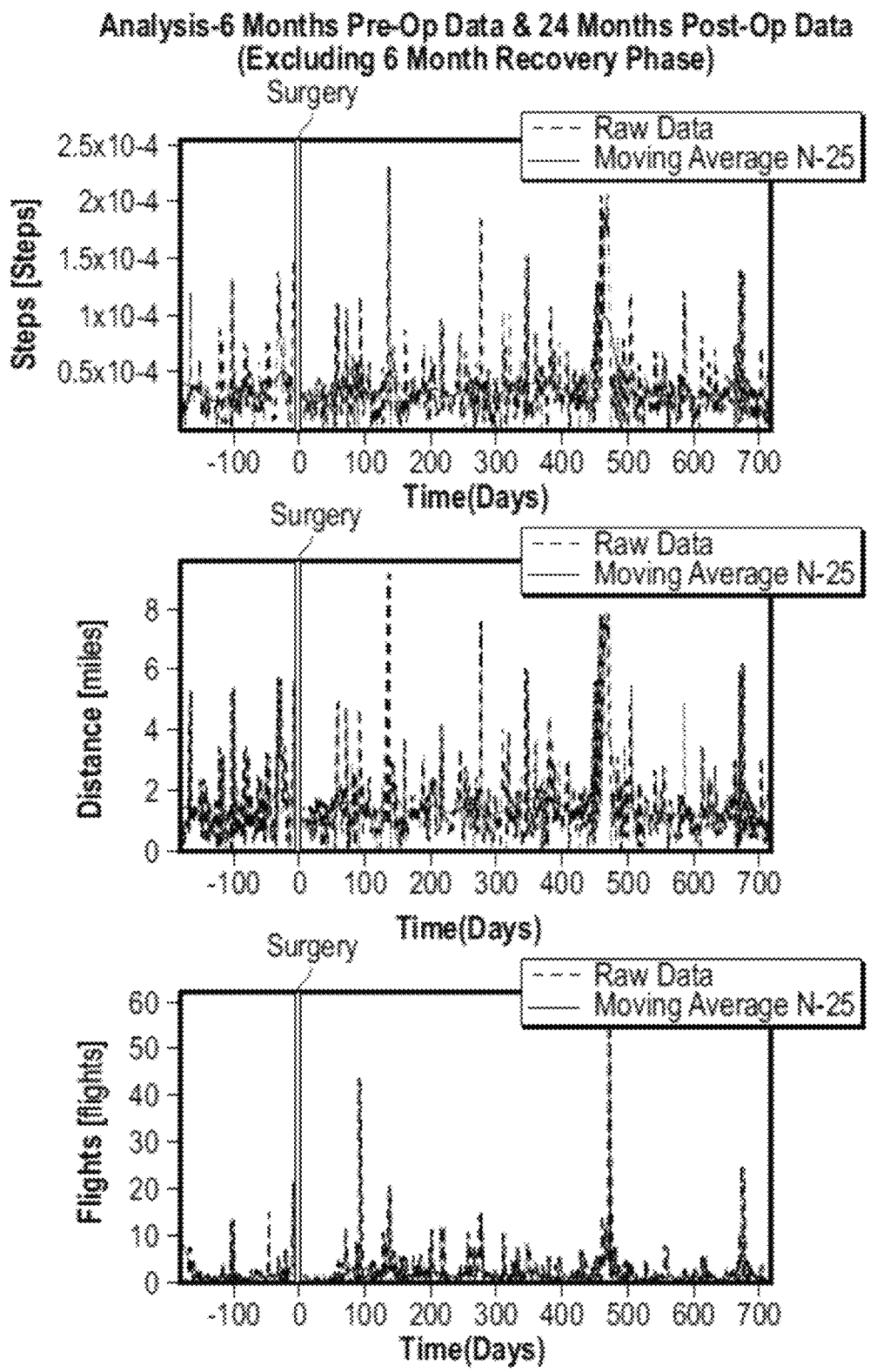
FIG. 4 depicts graphs illustrating the activity data, in accordance with aspects of the present disclosure.

FIG. 4 depicts graphs illustrating the activity data, in accordance with aspects of the present disclosure. Each graph shown in FIG. 4 shows the daily activity data (solid line) with a user-adjustable moving average (dashed line, 25 days in FIG. 4). The vertical line represents the date of surgery (all data to the left is pre-operative and to the right is post-operative).

Figure 5:
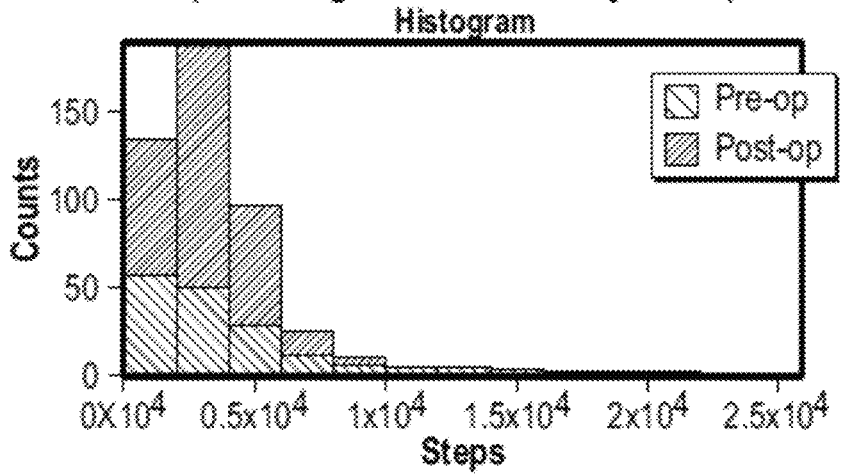
FIG. 5 depicts graphs illustrating the distribution of activity data, in accordance with aspects of the present disclosure.
Figure 5:
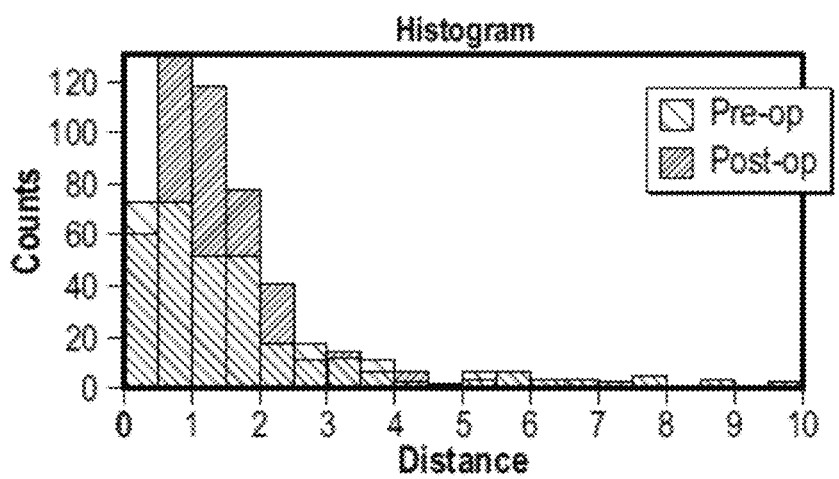
Figure 5:
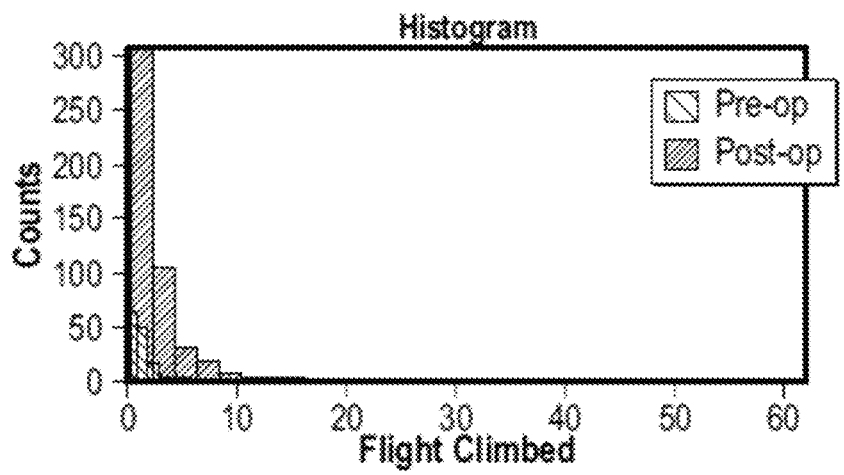

FIG. 5 depicts graphs illustrating the distribution of activity data, in accordance with aspects of the present disclosure. The histograms shown in FIG. 5 demonstrate the distribution of activity both pre- and post-operatively to allow for visual comparison of the activity distributions before and after surgery.

Figure 6:
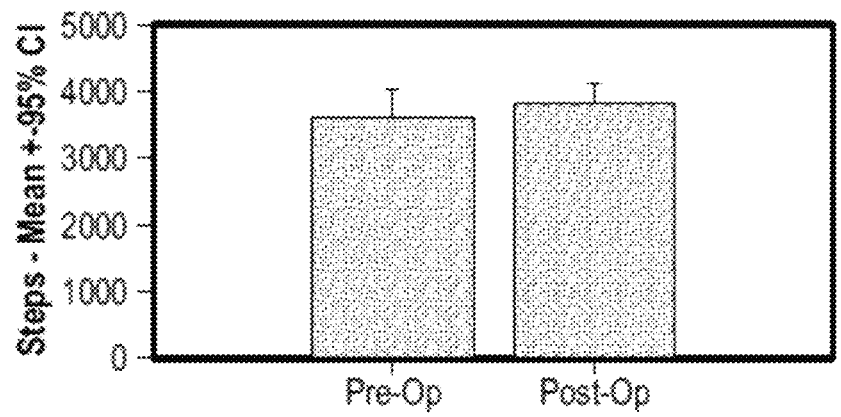
FIG. 6 depicts graphs illustrating the mean activity levels with error bars, in accordance with aspects of the present disclosure.
Figure 6:
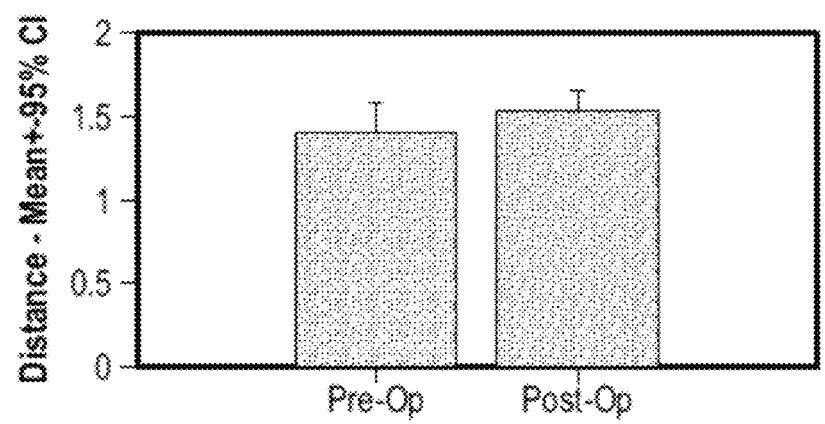
Figure 6:
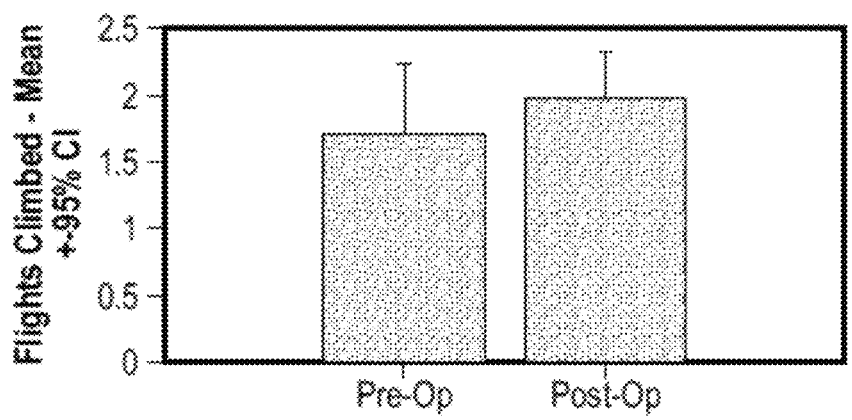

FIG. 6 depicts graphs illustrating the mean activity levels with error bars, in accordance with aspects of the present disclosure. The bar-graphs shown in FIG. 6 demonstrate mean pre- and post-operative activity levels with error bars demonstrating the 95% confidence interval around the estimated mean. A unpaired two-tailed t-test is used to determine the probability (p-value) that two independent samples from the pre-operative and post-operative distributions come from normal distributions with equal means. This p-value is reported above the bar graph.

Figure 7:
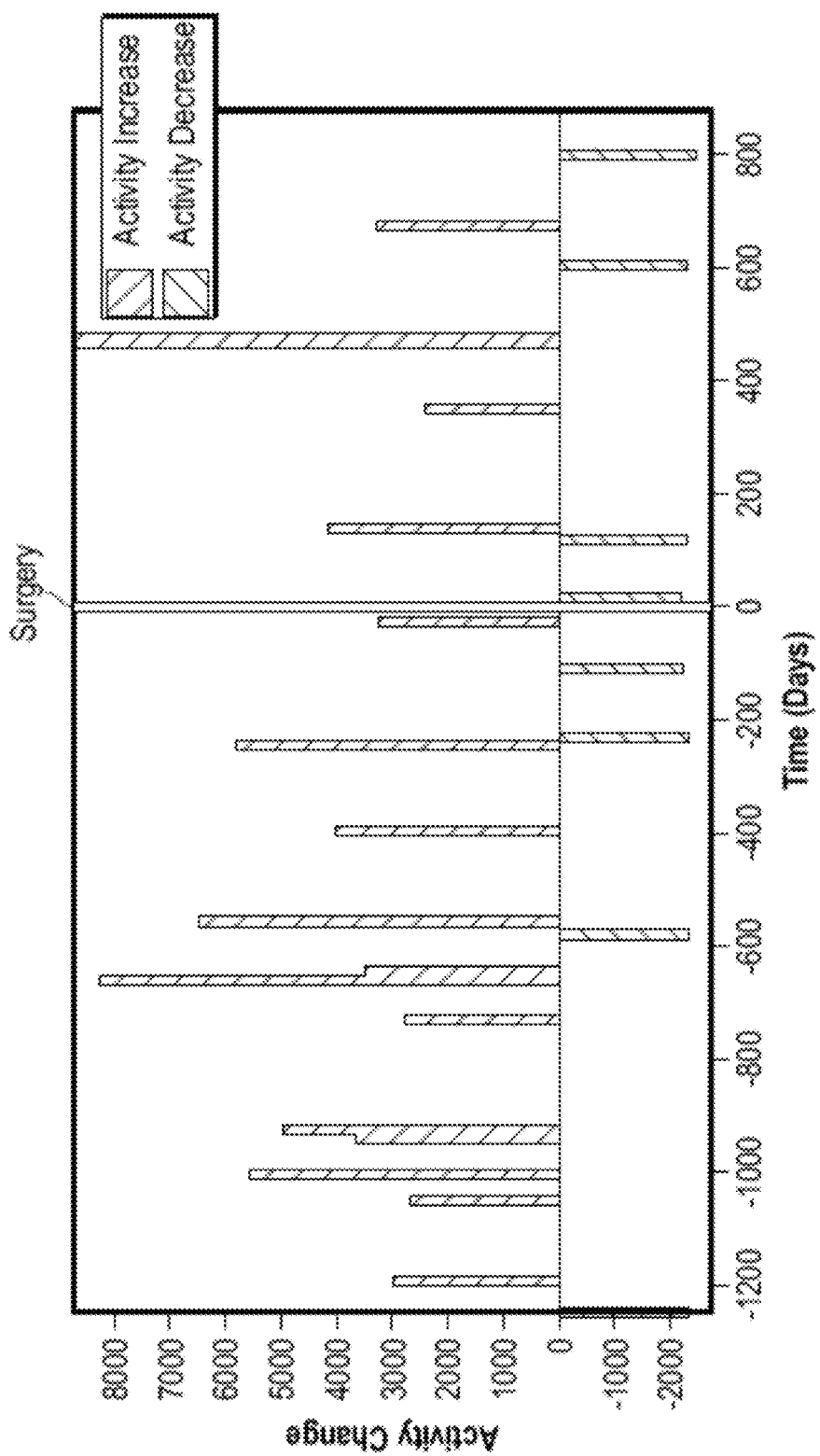
FIG. 7 depicts a graph illustrating the times of increased and decreased activity levels, in accordance with aspects of the present disclosure.

FIG. 7 depicts a graph illustrating the times of increased and decreased activity levels, in accordance with aspects of the present disclosure. In the graph shown in FIG. 7, the baseline activity is filtered with a moving-average (number of days is user selectable). High or low activity periods are identified as those that vary from the mean by >than 1 standard deviation (this could be made a user-selected variable). The height of the bars represents the average increase or decrease in activity relative to the mean activity baseline. The width of the bar represents the duration of the activity increase or decrease.

Figure 8:
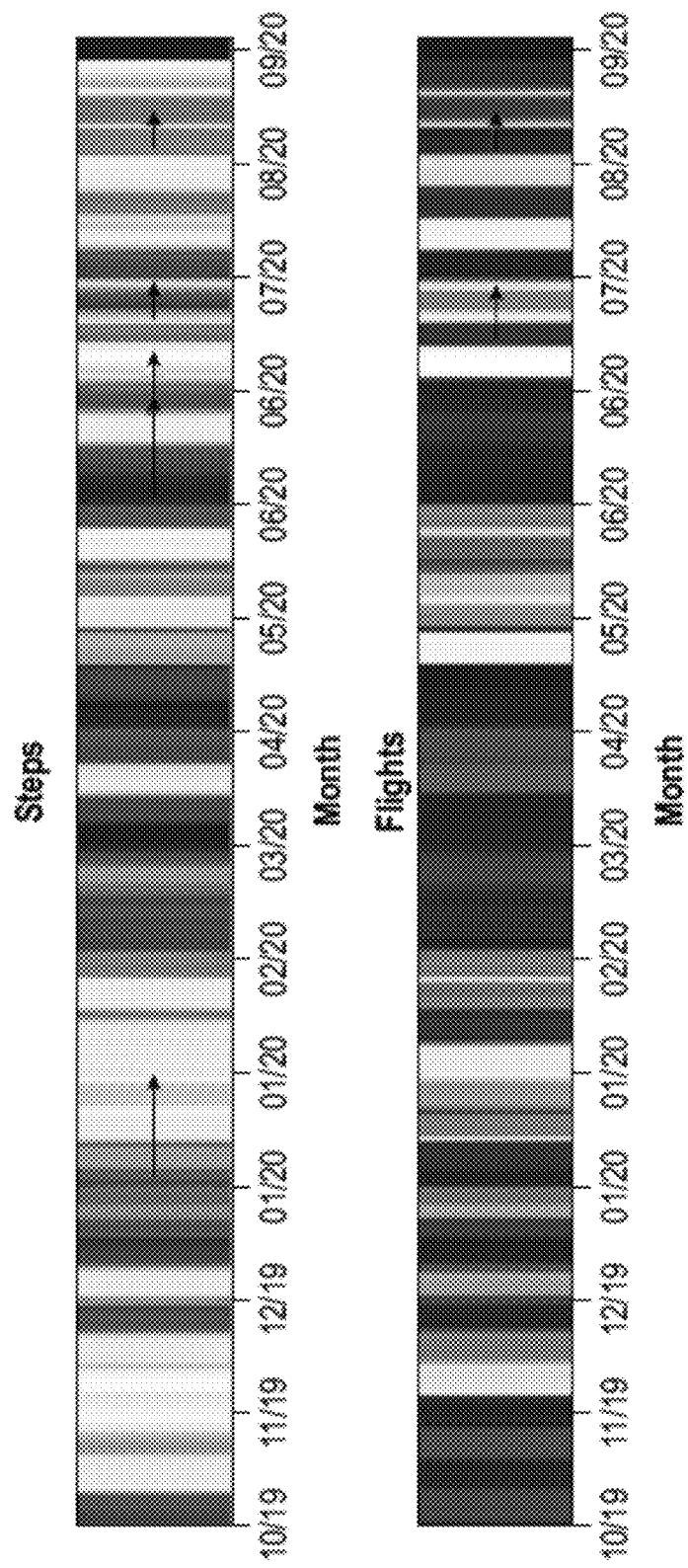
FIG. 8 depicts heat maps illustrating the levels of activity with overlaid arrows, in accordance with aspects of the present disclosure.

FIG. 8 depicts heat maps illustrating the levels of activity with overlaid arrows, in accordance with aspects of the present disclosure. In the heat maps of FIG. 8, overlaid arrows indicate periods of significant activity "ramp-up," where the length and size (thickness of line, size of arrowhead) correspond to the duration and slope of activity ramp-up. In FIG. 8, raw data was z-score normalized with respect to the pre-operative period, and then smoothed using a 7-day sliding window. Periods of significant activity ramp-up were identified with an optimization method with the following costs (e.g., findchangepts.m in MATLAB): (1) the number of "change points" (linear penalty weight for each number of change points); and (2) the sum of squared residuals of the linear fits of the data between the change points. It is noted that adding change points always decreases residual error. For example, if each point in the time series is a change point, then the error sum of squares diminished to zero. Hence, the weights for (1) are important to avoid overfitting. The weights for (1) may be determined in an iterative, data-driven fashion such that the minimum number of days between change points was above a threshold value, e.g., 3 days (as ramp up of activity spanning only a day or two may not be as interesting for this analysis).

Figure 9:
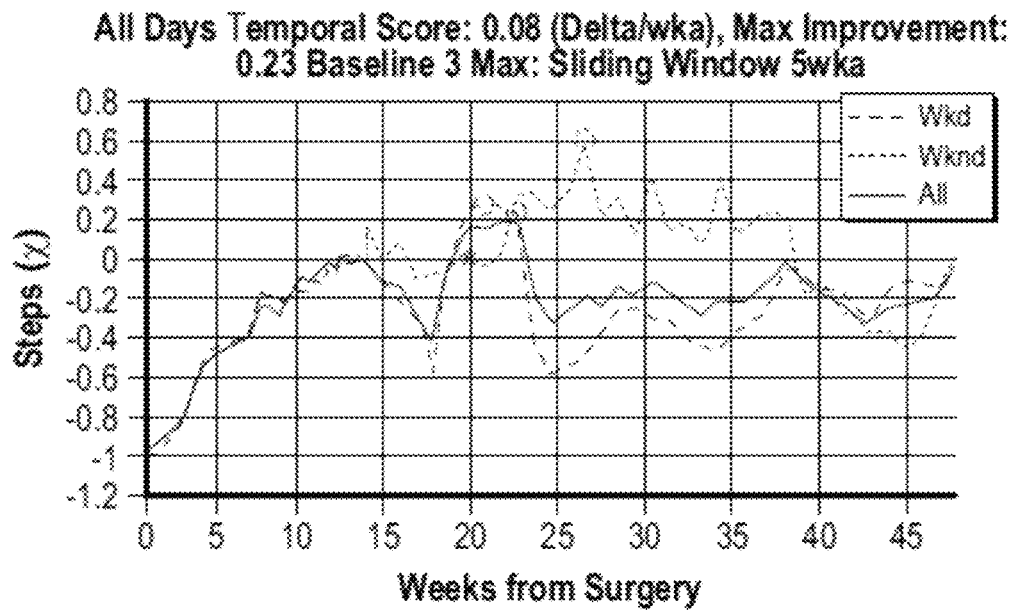
FIG. 9 depicts graphs illustrating the levels of steps and step sizes, in accordance with aspects of the present disclosure.
Figure 9:
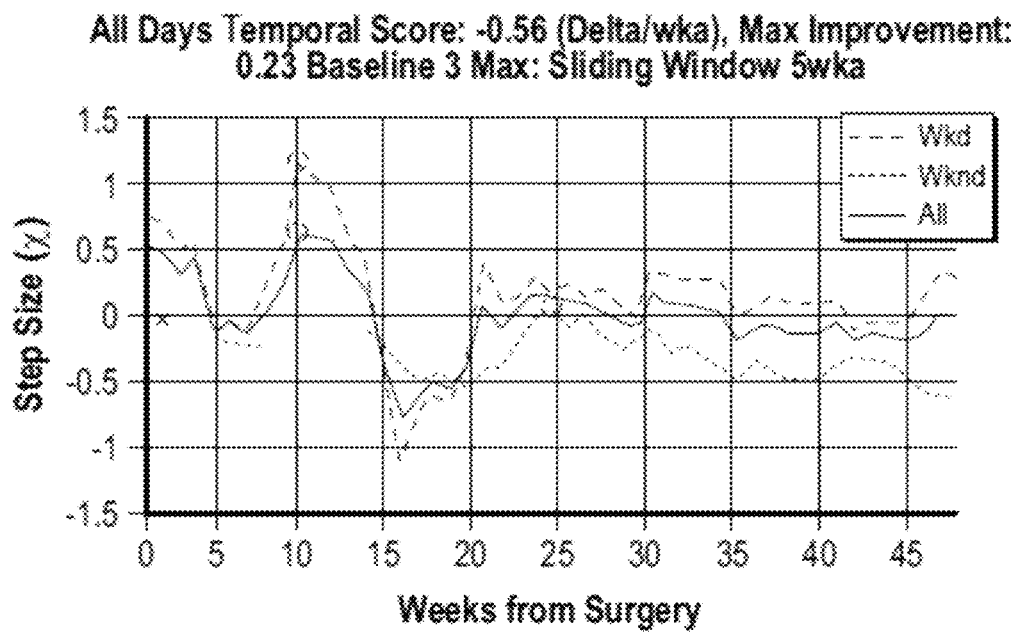
Figure 10:
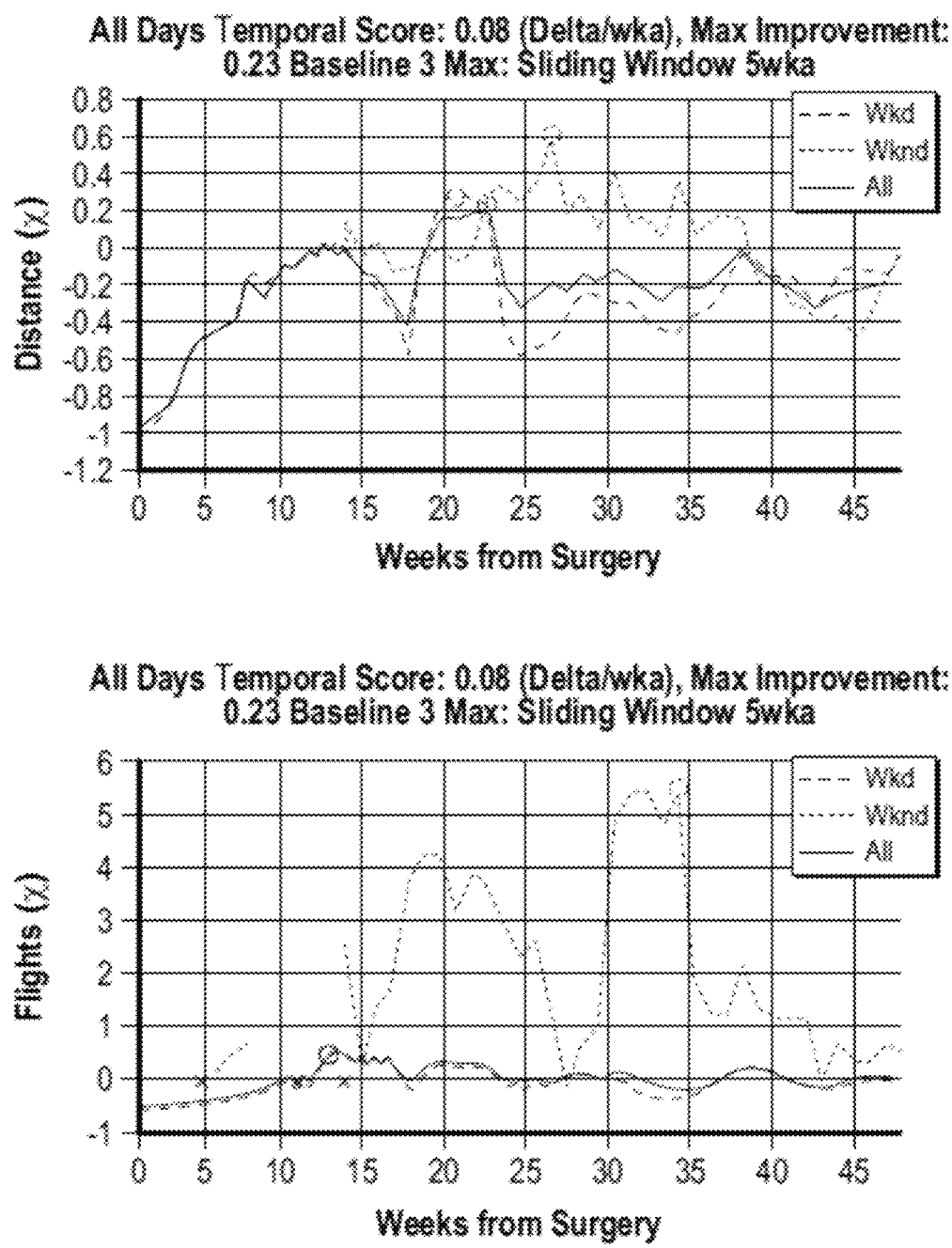
FIG. 10 depicts graphs illustrating the levels of distances and flights, in accordance with aspects of the present disclosure.

FIG. 9 depicts graphs illustrating the levels of steps and step sizes, in accordance with aspects of the present disclosure. FIG. 10 depicts graphs illustrating the levels of distances and flights, in accordance with aspects of the present disclosure. In the graphs of FIGS. 9 and 10, raw data were z-score normalized with respect to the pre-operative distribution, for each metric separately. X-axis indicates weeks from surgery. Values above 0 (y-axis) indicate daily level of activity at the pre-operative baseline. Within each subfigure, data was plotted separately for weekdays (dashed line), weekends (dotted line), and all together (solid line). Step size calculated as distance/steps. Data was then smoothed with a 7-day moving average. Days without data available were filled with NaN. In some embodiments, only the weekend activity data may be used in performing the analyses described herein. In other embodiments, only the weekday activity data may be used in performing the analyses described herein. In yet other embodiments, both the weekday activity data and the weekend activity data may be used in performing the analyses described herein.

Figure 11:
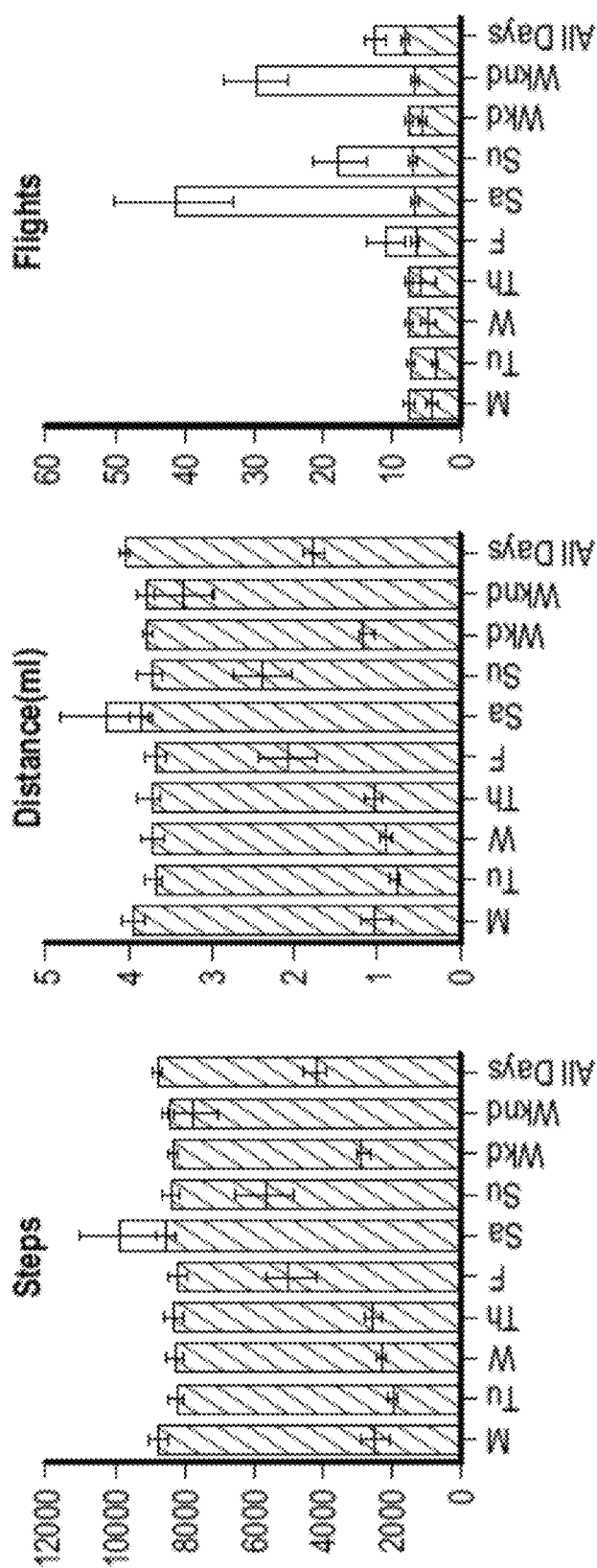
FIG. 11 depicts graphs illustrating the pre-op and post-op levels of steps, distances, and flights for each day of the week, weekdays, weekend days, and all days, in accordance with aspects of the present disclosure.

FIG. 11 depicts graphs illustrating the pre-op and post-op levels of steps, distances, and flights for each day of the week, weekdays, weekend days, and all days, in accordance with aspects of the present disclosure. In FIG. 11, data is further stratified for pre-(shaded) and post-operative (blank) period, and the error bars indicate the standard error of the mean (SEM).

Figure 12:
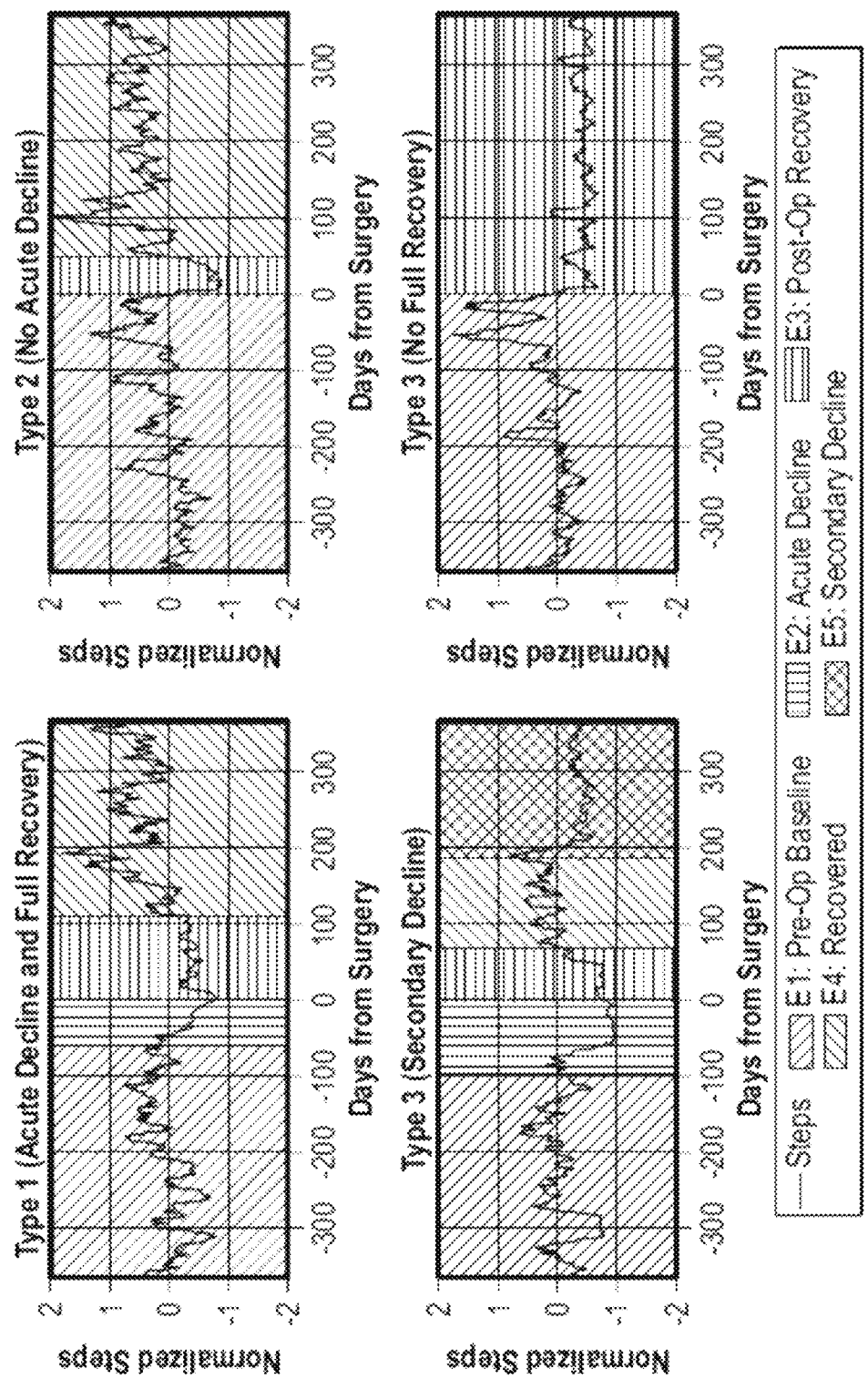
FIG. 12 depicts graphs illustrating the pre-op and post-op levels of steps in different types of scenarios including visual indications of the identified temporal windows (epochs), in accordance with aspects of the present disclosure.

FIG. 12 depicts graphs illustrating the pre-op and post-op levels of steps in different types of scenarios including visual indications of the identified temporal windows (epochs), in accordance with aspects of the present disclosure. Based on the time series of daily level of steps in the pre-operative period, the system 106 may automatically detect pre-defined "epochs": 1) Epoch 1 is their pre-operative baseline state, where the patient was in their usual state of health (either healthy or chronically-debilitated); 2) Epoch 2 represents an acute decline (if any) relative to their baseline, and represents the state the patient would have been without intervention; 3) Epoch 3 is the post-surgical recovery period when the patients are recovering from acute surgical pain, undergoing physical therapy/rehabilitation; 4) Epoch 4 represents a return to their new post-operative baseline level of activity, which may be on par with Epoch 1 or improved; 5) Epoch 5 was identified in patient who had a secondary decline after a period of full recovery from the surgery. This may be due to re-aggravation of their injury, or a different disease state that may interfere with their mobility. All subjects have epochs 1 and 3, whereas epochs 2, 4, and 5 depend on their specific pre-operative pattern of activity. Epochs were identified after z-score normalized raw data with respect to pre-operative distribution and smoothing with a 7-day sliding window. E2 was identified if there was a period leading up to surgery (day=0) with mean steps <0 sustained for >10 days, with minimum steps <0.5. E4 was identified if there was a period in the post-operative period with mean steps >−0.25 sustained for >10 days. E5 was identified only if E4 was found, using the same criteria as for E2. In other embodiments, any combination of mean steps, minimum steps, or sustained period may be used. In embodiments, E2 and E5 are configured to begin on a zero-crossing on a z-score normalized graph (e.g., where the graph crosses from a positive value to a negative value), and E4 is configured to begin on a zero-crossing on a z-score normalized graph (e.g., where the graph crosses from a negative value to a positive value).

Figure 13:
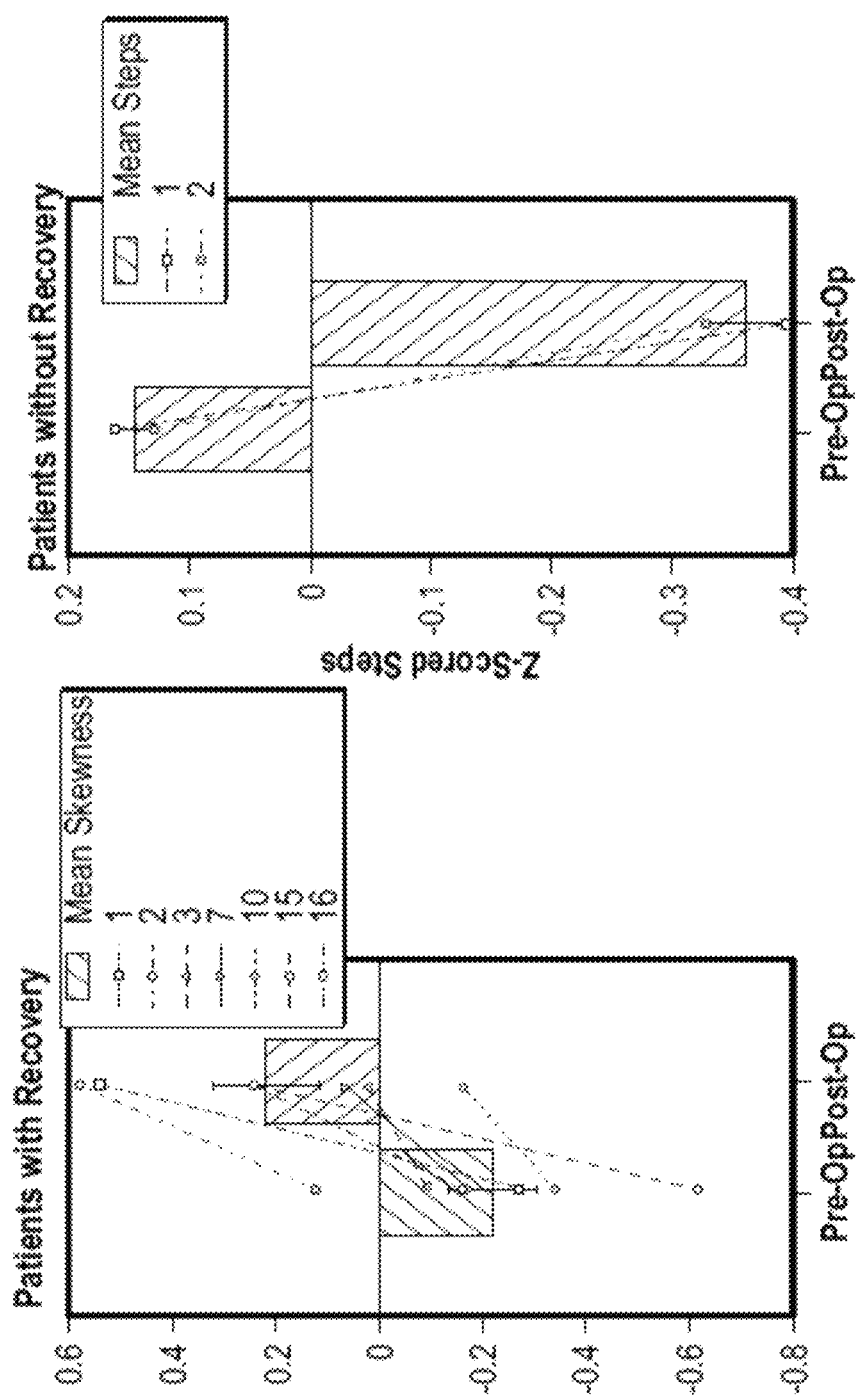
FIG. 13 depicts graphs illustrating comparisons of pre-op and post-op steps, in accordance with aspects of the present disclosure.
Figure 14:
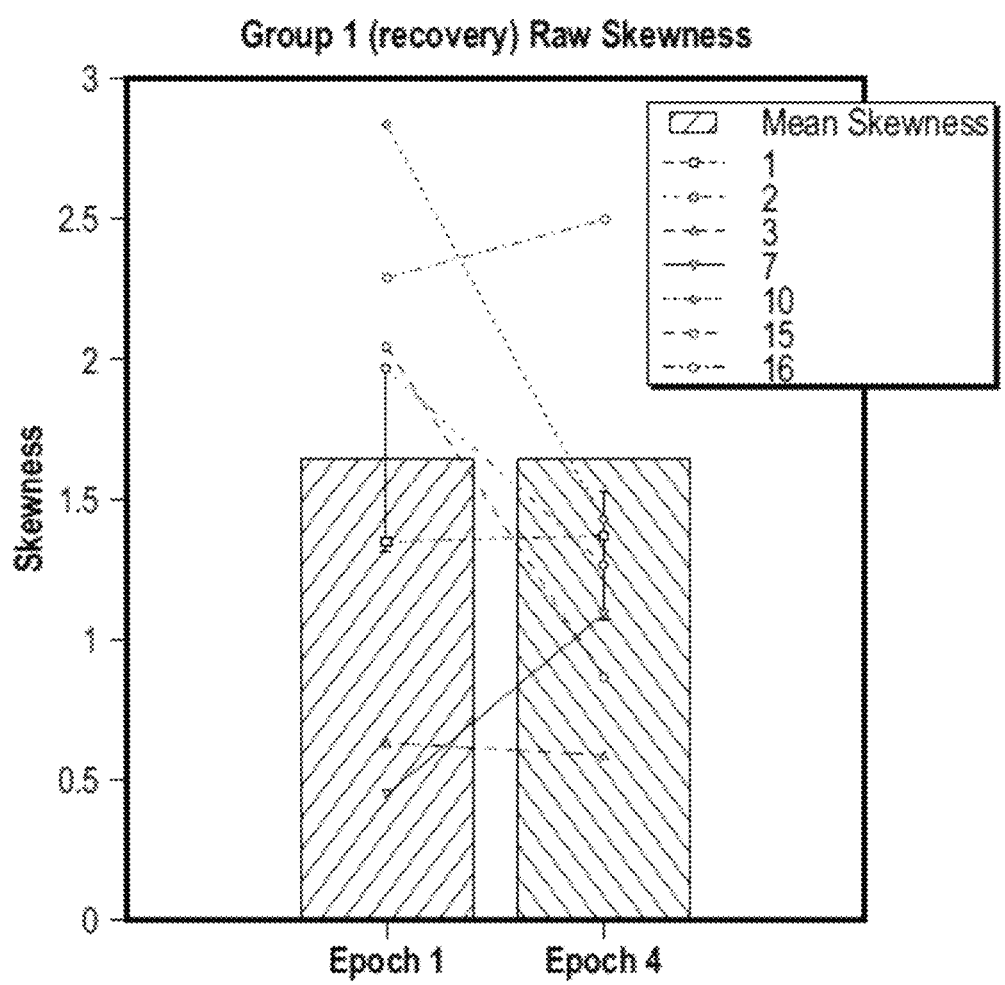
FIG. 14 depicts a graph illustrating a comparison of the skewness of pre-op and post-op distribution of steps, in accordance with aspects of the present disclosure.

FIG. 13 depicts graphs illustrating comparisons of pre-op and post-op steps, in accordance with aspects of the present disclosure, and FIG. 14 depicts a graph illustrating a comparison of the skewness of pre-op and post-op distribution of steps, in accordance with aspects of the present disclosure.

The graphs of FIG. 13 show a comparison of the mean daily steps between the Epoch 2 vs. Epoch 4. If E2 is not available or identified, E1 may be used, and if E4 is not available or identified, E3 may be used. The illustrated comparison measures the degree of improvement in daily steps following surgical intervention, comparing between the state the patient would have been without surgery (E2 or E1) vs. after surgery (E4 or E3). Data points are plotted separately for patients with a full recovery (E4 following E3 in post-operative period) and those without (only E3), using normalized data for visualization. Using raw steps instead may also provide qualitatively identical results.

The graph of FIG. 14 shows a comparison of the skewness of the pre- vs post-surgical distributions of daily steps. Analysis was conducted as for mean daily steps, except without z-score normalization. Moreover, this comparison was conducted for data between E1 and E4. The underlying hypothesis here was that the mobility data of a healthy person would demonstrate a positive skewness, as healthy people are able to ramp up their activities on certain days. Indeed, we found that a full recovery (as determined by time series analysis) was characterized by an increase in mean daily steps as well as skewness, or an increase in mean daily steps without an increase in skewness. Although the relative importance of mean vs. skewness remains to be determined with a larger data set, increases in mean (from pre- to post-op) is likely negatively correlated with increased in skewness.

Assisting Decision of Whether to Undergo Surgery

Figure 15:
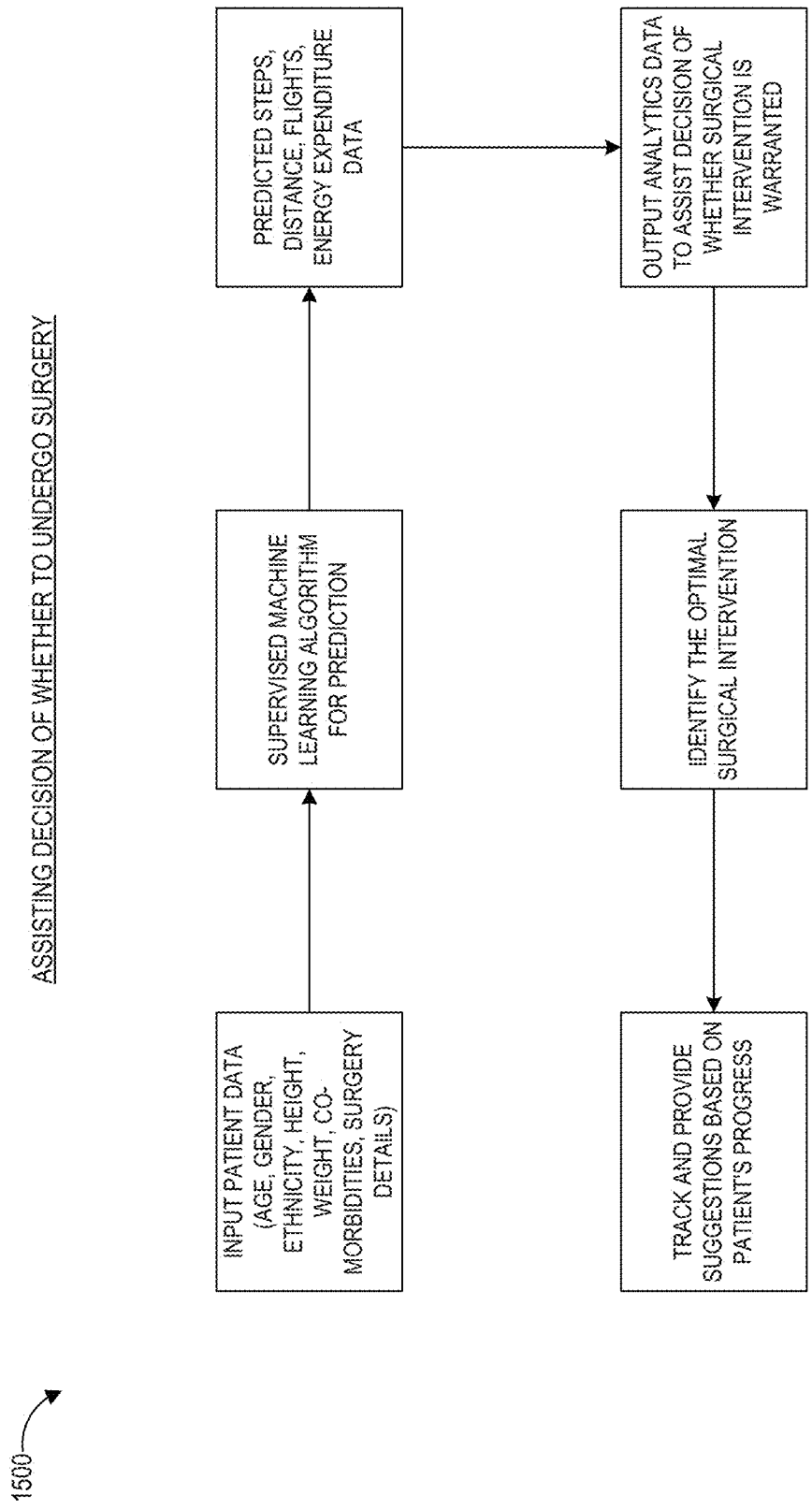
FIG. 15 depicts a block diagram illustrating an example work flow of assisting a decision of whether to undergo a surgical intervention, in accordance with aspects of the present disclosure.

FIG. 15 depicts an illustrative routine 1500 for assisting the decision of whether to undergo a surgery or other medical intervention in accordance with aspects of the present disclosure. As shown in FIG. 15, the routine 1500 may include (i) collecting input patient data (e.g., sex, age, symptoms, activity data, details of the surgery that the patient may undergo to improve her conditions, etc.), (ii) identifying machine learning algorithms to be used to determine predicted post-operative activity data (e.g., step count, step size, travel distance, flights of stairs climbed, calorie count, etc.), (iii) determining the predicted post-operative activity data, (iv) outputting analytics data to assist decision of whether a surgical intervention is warranted, (v) identifying the optimal surgical intervention (e.g., by comparing the predicted post-operative activity data for multiple surgeries or types of surgeries), and (vi) tracking and providing suggestions based on the patient's progress after the surgical intervention.

Machine learning algorithm (MLA) is developed in parallel to predict individual patient's outcome after a surgical intervention. The algorithm undergoes supervised learning by inputting known variables and this will be used to predict the patient's activity levels after surgery. With this information, the physician and the patient can the make a decision to undergo surgery jointly based on predicted activity level as shown in FIG. 15. For instance, those patients who has not yet undergone surgery (e.g. one level lumbar discectomy) for radiculopathy, their activity levels and ORBIT metric post-operatively will be predicted and this will be used to guide the surgery decision. Using MLA, the patient's post-operative physical levels will be accurately predicted. MLA will be trained using the input of baseline patient characteristics (age, sex, BMI, medical conditions, bone density, etc.) and the prior examples of pre-operative and post-operative physical activity data from the patients who have already undergone surgery. Using MLA, the surgeon will be able to reliably inform a 40 year-old lady about their post-operative course, after undergoing one level lumbar discectomy, based on thousands of patients with similar baseline health history and baseline activity level. Surgical approach, whether the surgery is done through minimally invasive or through open approach, will also be factored into the formation of MLA, therefore, both the patient and the doctor will be able to choose the optimal surgical intervention.

Example Routine for Performing Pre-Operative Analysis of Patient Data

Figure 16:
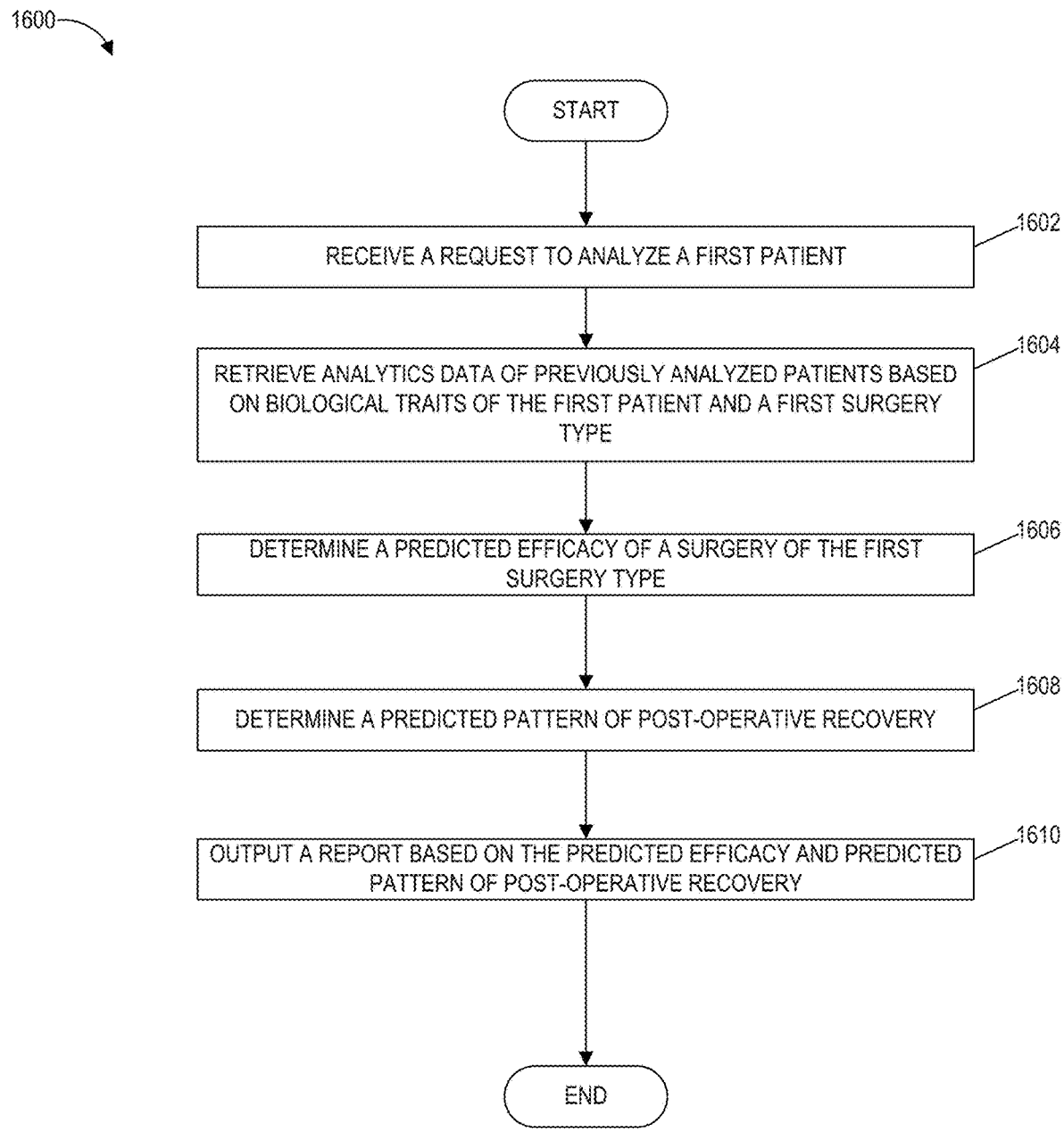
FIG. 16 is a flowchart of an example process for performing a pre-op analysis of patient data, in accordance with aspects of the present disclosure.

FIG. 16 depicts an illustrative routine 1600 for performing pre-operative analysis of patient data in accordance with aspects of the present disclosure. The routine 1600 may be carried out, for example, by the data analysis service 130 and/or the report generation service 150 or one or more other components of the medical intervention analytics system 106 described herein. For convenience, some or all of the steps of the routine 1600 are described as being performed by the system 106. For example, the system 106 may include one or more hardware computing devices and non-transitory physical computer storage storing instructions that, when executed by the one or more hardware computing devices, cause the one or more hardware computing devices to perform the steps of the routine 1600.

The routine 1600 begins at block 1602, at which the system 106 receives a request to analyze a first patient.

At block 1604, the system 106 retrieves analytics data of previously analyzed patients (e.g., as illustrated in FIG. 3) based on the biological traits data associated with the first patient and a first surgery type (e.g., a type of surgery that is being considered for the first patient).

At block 1606, the system 106 determines a predicted efficacy score of a first surgery of the first surgery type.

At block 1608, the system 106 determines a predicted pattern of post-operative recovery.

At block 1610, the system 106 outputs a report based on the predicted efficacy and predicted pattern of post-operative recovery. For example, the report may be presented to the user computing device 102 via a mobile application or a browser application in the form of a user interface that includes a user interface element indicative of the predicted efficacy and another user interface element indicative of the predicted pattern of post-operative recovery. The routine 1600 may then end.

The routine 1600 can include fewer, more, or different blocks than those illustrated in FIG. 16 and/or one or more blocks illustrated in FIG. 16 may be modified, omitted, or switched without departing from the scope of the description. Moreover, it will be appreciated by those skilled in the art and others that some or all of the functions described in this disclosure may be embodied in software executed by one or more processors of the medical intervention analytics system 106 and/or the user computing device 102 disclosed herein.

Example Routine for Outputting Visually Distinguished Temporal Windows

Figure 17:
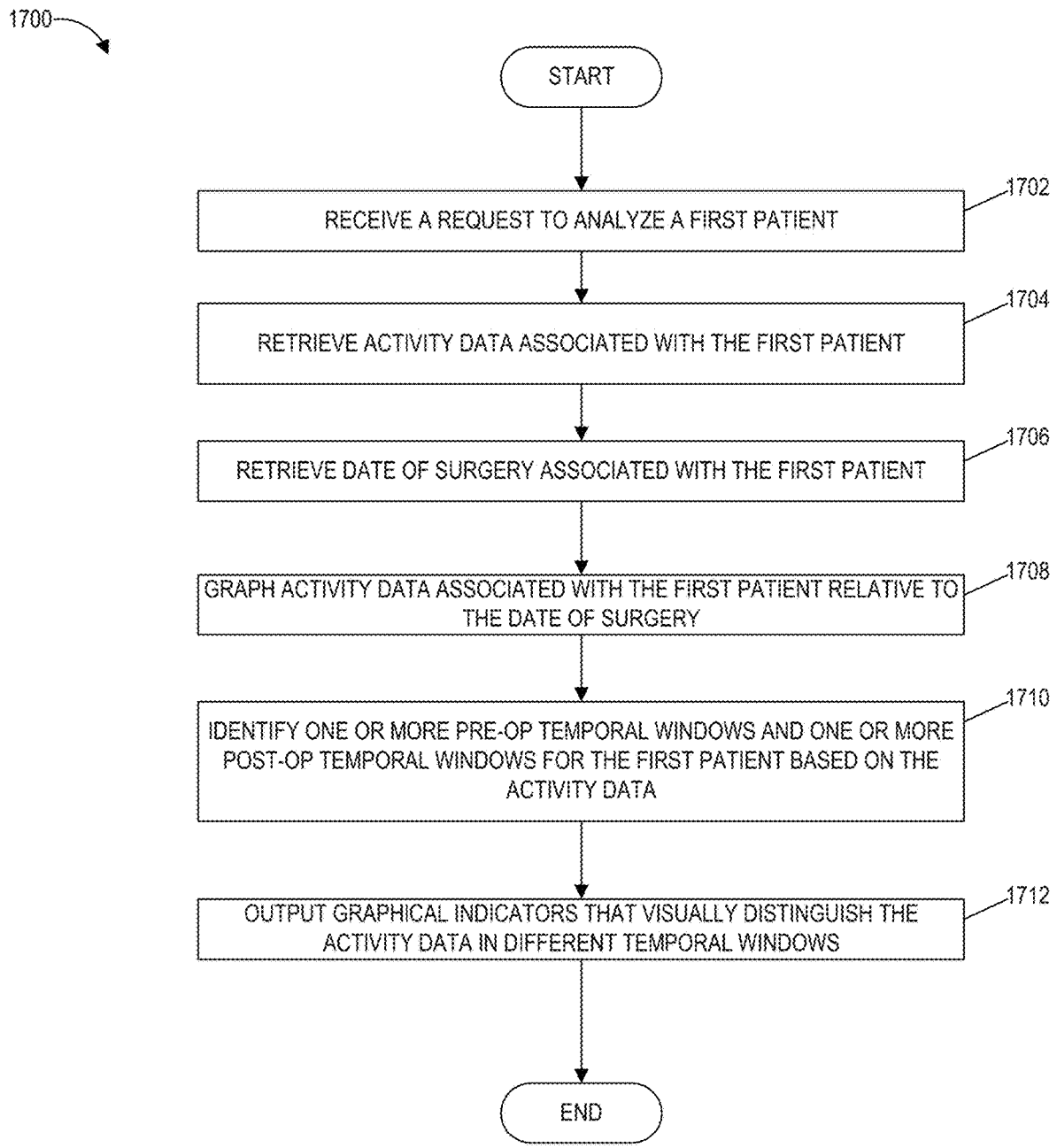
FIG. 17 is a flowchart of an example process for outputting visually distinguished temporal windows, in accordance with aspects of the present disclosure.

FIG. 17 depicts an illustrative routine 1700 for outputting visually distinguished temporal windows in accordance with aspects of the present disclosure. The routine 1700 may be carried out, for example, by the data analysis service 130 and/or the report generation service 150 or one or more other components of the medical intervention analytics system 106 described herein. For convenience, some or all of the steps of the routine 1700 are described as being performed by the system 106. For example, the system 106 may include one or more hardware computing devices and non-transitory physical computer storage storing instructions that, when executed by the one or more hardware computing devices, cause the one or more hardware computing devices to perform the steps of the routine 1700.

The routine 1700 begins at block 1702, at which the system 106 receives a request to analyze a first patient.

At block 1704, the system 106 retrieves activity data associated with the first patient.

At block 1706, the system 106 retrieves the date of surgery associated with the first patient.

At block 1708, the system 106 graphs the activity data associated with the first patient relative to the date of surgery. For example, a portion of the activity data that precedes the surgery date may be plotted on the left side of the graph (e.g., to the left of the position indicative of the surgery date), and the remaining portion of the activity data that follows the surgery date may be plotted on the right side of the graph (e.g., to the right of the position indicative of the surgery date).

At block 1710, the system 106 identifies one or more pre-operative temporal windows and one or more post-operative temporal windows for the first patient based on the activity data. The techniques for identifying the temporal windows are described in greater detail below with reference to FIG. 18.

At block 1712, the system 106 outputs graphical indicators that visually distinguish the activity in different temporal windows. For example, each section of the graph (or the plotted data point(s)) corresponding to a different temporal window may be in a different color (or different shading, boldness, solid/dashed lines, etc.). The routine 1700 may then end.

The routine 1700 can include fewer, more, or different blocks than those illustrated in FIG. 17 and/or one or more blocks illustrated in FIG. 17 may be modified, omitted, or switched without departing from the scope of the description. Moreover, it will be appreciated by those skilled in the art and others that some or all of the functions described in this disclosure may be embodied in software executed by one or more processors of the medical intervention analytics system 106 and/or the user computing device 102 disclosed herein.

Example Routine for Identifying Temporal Windows Based on Patient Activity Data

Figure 18:
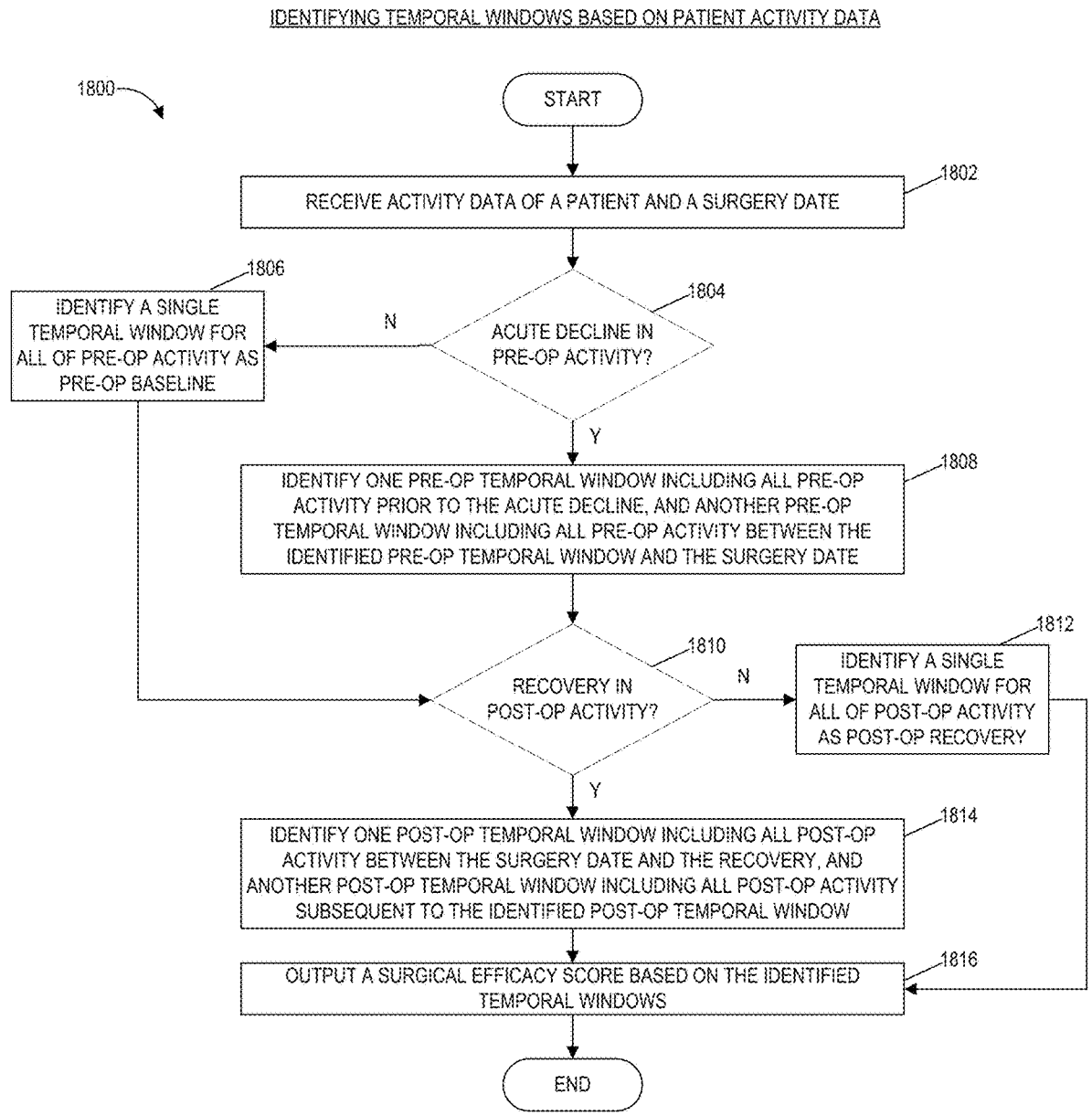
FIG. 18 is a flowchart of an example process for identifying temporal windows based on patient activity data, in accordance with aspects of the present disclosure.

FIG. 18 depicts an illustrative routine 1800 for identifying temporal windows based on patient activity data in accordance with aspects of the present disclosure. The routine 1800 may be carried out, for example, by the data analysis service 130 and/or the report generation service 150 or one or more other components of the medical intervention analytics system 106 described herein. For convenience, some or all of the steps of the routine 1800 are described as being performed by the system 106. For example, the system 106 may include one or more hardware computing devices and non-transitory physical computer storage storing instructions that, when executed by the one or more hardware computing devices, cause the one or more hardware computing devices to perform the steps of the routine 1800.

The routine 1800 begins at block 1802, at which the system 106 receives the activity data of a patient and a date associated with a surgery undergone by the patient.

At block 1804, the system 106 determines whether an acute decline is detected in the pre-operative portion of the activity data. For example, an acute decline may be detected by determining whether the activity (e.g., step count, or another value described herein) remains below a threshold average level (e.g., zero in z-score normalized steps) for a threshold period of time (e.g., 10 days) while reaching at least a threshold minimum level (e.g., −0.5 in z-score normalized steps). In another example, any combination of these criteria (threshold average level, threshold period of time, and/or threshold minimum level) may be used to detect an acute decline.

If the system 106 determines that an acute decline is not detected, the routine 1800 proceeds to block 1806, where the system 106 identifies a single temporal window ("pre-operative baseline" period) for all of the pre-operative portion of the activity data. Otherwise, the routine 1800 proceeds to block 1808.

At block 1808, the system 106 identifies one pre-operative temporal window ("pre-operative baseline" period) including all pre-operative activity prior to the acute decline, and another pre-operative temporal window ("acute decline" period) including all pre-operative activity between the identified pre-operative temporal window and the surgery date.

At block 1810, the system 106 determines whether a recovery is detected in the post-operative portion of the activity data. For example, a recovery may be detected by determining whether the activity (e.g., step count, or another value described herein) above a threshold average level (e.g., −0.25 in z-score normalized steps) for a threshold period of time (e.g., 10 days) while reaching at least a threshold maximum level (e.g., 0.25 in z-score normalized steps). In another example, any combination of these criteria (threshold average level, threshold period of time, and/or threshold maximum level) may be used to detect a recovery.

If the system 106 determines that a recovery is not detected, the routine 1800 proceeds to block 1812, where the system 106 identifies a single temporal window ("post-operative recovery" period) for all of the post-operative portion of the activity data. Otherwise, the routine 1800 proceeds to block 1814.

At block 1814, the system 106 identifies one post-operative temporal window ("post-operative recovery" period) including all post-operative activity between the surgery date and the detected recovery, and another pre-operative temporal window ("recovered" period) including all post-operative activity after the identified post-operative temporal window.

At block 1816, the system 106 outputs a surgical efficacy score based on the identified temporal windows. For example, the surgical efficacy score may be calculated by dividing the average step count in the "recovered" period by the average step count in the "acute decline" period. As another example, the surgical efficacy score may be calculated by dividing the average step count in the "post-operative recovery" period (e.g., if the "recovered" period is not identified) by the average step count in the "pre-operative baseline" period (e.g., if the "acute decline" period is not identified). The routine 1800 may then end.

The routine 1800 can include fewer, more, or different blocks than those illustrated in FIG. 18 and/or one or more blocks illustrated in FIG. 18 may be modified, omitted, or switched without departing from the scope of the description. For example, although not shown in FIG. 18, the system 106 may identify another temporal window subsequent to the "recovered" period, in response to detecting another acute decline (e.g., using the techniques described above) subsequent to the detected recovery. The identified temporal window may include the detected post-operative acute decline and the activity data subsequent to the post-operative acute decline. Moreover, it will be appreciated by those skilled in the art and others that some or all of the functions described in this disclosure may be embodied in software executed by one or more processors of the medical intervention analytics system 106 and/or the user computing device 102 disclosed herein.

Comparison of Temporal Windows

The system 106 may compare the lengths of E3 for different surgeries (or any other parameters associated with the surgeries, such as surgeon, medical device, device manufacturer, surgery length, time of day, pre-existing conditions, patient biological trait, etc.) to determine which surgery or medical device shortens E3. Such determination may be included in a report.

The system 106 may compare the amplitudes of E4 for different surgeries (or any other parameters associated with the surgeries, such as surgeon, medical device, device manufacturer, surgery length, time of day, pre-existing conditions, patient biological trait, etc.), determine which surgery or medical device results in higher E4. Such determination may be included in a report.

The system 106 may compare the efficacy (e.g., E4 or E3 divided by E2 or E1) for different surgeries (or any other parameters associated with the surgeries, such as surgeon, medical device, device manufacturer, surgery length, time of day, pre-existing conditions, patient biological trait, etc.) to determine which surgery or medical device results in greater efficacy. Such determination may be included in a report.

Example Architecture of Computing System

Figure 19:
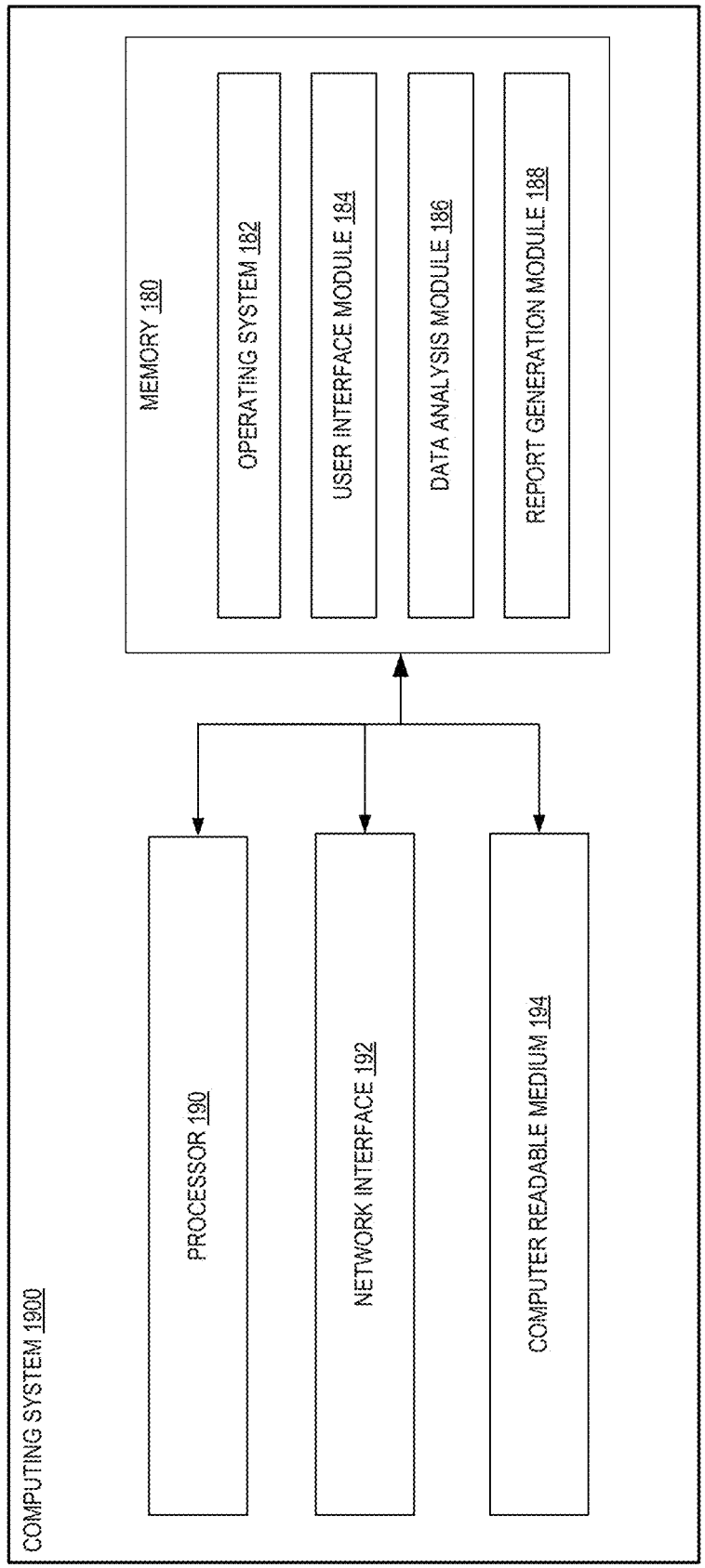
FIG. 19 depicts a general architecture of a computing system usable to implement one or more components described herein in accordance with aspects of the present disclosure.

FIG. 19 depicts an example architecture of a computing system 1900 that can be used to perform one or more of the techniques described herein or illustrated in FIGS. 1-18. The general architecture of the computing system 1900 depicted in FIG. 19 includes an arrangement of computer hardware and software modules that may be used to implement one or more aspects of the present disclosure. The computing system 1900 may include many more (or fewer) elements than those shown in FIG. 19. It is not necessary, however, that all of these elements be shown in order to provide an enabling disclosure. For example, the computing system 1900 may be used to implement one or more of the elements described herein, including the data analysis service 130, the report generation service 150, and/or the user computing devices 102.

As illustrated, the computing system 1900 includes a processor 190, a network interface 192, and a computer-readable medium 194, all of which may communicate with one another by way of a communication bus. The network interface 192 may provide connectivity to one or more networks or computing systems. The processor 190 may thus receive information and instructions from other computing systems or services via the network 104 illustrated in FIG. 1.

The processor 190 may also communicate with memory 180. The memory 180 may contain computer program instructions (grouped as modules in some embodiments) that the processor 190 executes in order to implement one or more aspects of the present disclosure. The memory 180 may include RAM, ROM, and/or other persistent, auxiliary, or non-transitory computer-readable media. The memory 180 may store an operating system 182 that provides computer program instructions for use by the processor 190 in the general administration and operation of the computing system 1900. The memory 180 may further include computer program instructions and other information for implementing one or more aspects of the present disclosure. For example, in one embodiment, the memory 180 includes a user interface module 184 that generates user interfaces (and/or instructions therefor) for display upon a user computing device (e.g., user computing device 102 of FIG. 1), e.g., via a navigation and/or browsing interface such as a browser or application installed on the user computing device. In addition, the memory 180 may include or communicate with one or more data stores.

In addition to and/or in combination with the user interface module 184, the memory 180 may include a data analysis module 186 and a report generation module 188 that may be executed by the processor 190. In one embodiment, the data analysis module 186 and the report generation module 188 collectively implement various aspects of the present disclosure, e.g., those illustrated in FIGS. 1-18 or described with reference to FIGS. 1-18.

Although a single processor, a single network interface, a single computer-readable medium, and a single memory are illustrated in the example of FIG. 19, in other implementations, the computing system 1900 can have a multiple of one or more of these components (e.g., two or more processors and/or two or more memories).

Surgeries and Other Types of Interventions

Although surgery is used as an example in some embodiments described herein, the techniques described in the present disclosure are not limited to surgeries and can be applied, in other embodiments, to any other types of treatments, procedures, or interventions.

Processed Activity Data

Although processed activity data (e.g., step count, step size, calorie count, flights climbed, etc.) is described in some embodiments as being generated by the patients' smartphones (e.g., by a mobile application installed on the smartphones) and provided to the system 106, in other embodiments, such processed activity data may be generated by the system 106 or another server based on raw data captured by the patients' smartphones (e.g., accelerometer data, gyroscope data, magnetometer data, etc., or any combination thereof).

Retrieving and Visualizing Analytics Data in Patient-Trait-Specific and Intervention-Specific Manner Based on the information associated with a given patient, the system 106 may filter the previously generated analytics data, and generate another set of analytics data for presentation to the patient. For example, the system 106 may determine that the patient is female, belongs to a 50-60 age group, and is considering a spine surgery. In response, the system 106 may filter the analytics data for female, 50-60 age group, and spine surgery, where the filtered analytics data indicate how other female patients in the age group who underwent a spine surgery performed before and after the surgery. Using this filtered data, the system 106 may newly generate analytics data for the patient. This newly generated analytics data may include a efficacy score associated with one or more types of spine surgery (e.g., by averaging the efficacy scores of the other female patients in the age group), and a respective predicted pattern of recovery (e.g., mobility levels) for each medical intervention. Based on the newly generated analytics data, a visual report may be generated for presentation to the patient and/or another user evaluating the medical intervention options on behalf of the user. Although this example only used gender and age group, any number of patient traits can be used in filtering the previously generated analytics data and/or generating the new analytics data for the patient. Also, although this example is used for providing analytics data for a new patient, in other embodiments, similar techniques may be used to compare the efficacy scores of various other criteria that may affect the outcome (e.g., medical practitioner, medical intervention date, medical device used, medical device manufacturer, medical intervention duration, level of invasiveness, medical intervention time of day, etc.) and/or any other combination of patient traits using existing patients' data. For example, a report comparing multiple medical practitioners, multiple medical devices, multiple medical device manufacturers, multiple medical intervention durations, multiple levels of invasiveness, and/or multiple medical intervention times of day can be generated and presented to the user. In some embodiments, predicted pattern of post-operative recovery can be generated for an existing patient who has already undergone a medical intervention.

Example Implementations (EIs)

Some enumerated example implementations (EIs) are provided in this section, without limitation.

EI 1: A system for providing analytics relating to patients and surgeries, the system comprising: a data repository storing analytics data associated with one or more patients; and a data analysis service comprising computer hardware, wherein the data analysis service is configured to at least: receive a first request to analyze a plurality of patients, wherein the first request includes (i) biological traits data associated with the plurality of patients, (i) step count data generated by a plurality of respective user computing devices associated with the plurality of patients, and (iii) surgery data associated with the plurality of patients; and for each respective patient of the plurality of patients: identify a set of temporal windows based at least in part on the step count data associated with the respective patient; select, from the set of temporal windows, a first temporal window prior to a surgery date associated with the respective patient and a second temporal window subsequent to the surgery date; generate a surgical efficacy score based at least in part on a comparison of first step count data associated with the first temporal window and second step count data associated with the second temporal window; and store the surgical efficacy score in association with (a) at least a portion of the biological traits data associated with the respective patient and (b) at least a portion of the surgery data associated with the respective patient, such that the surgical efficacy score associated with the respective patient is retrievable in a biological-trait-specific and surgery-specific manner, wherein the data analysis service is further configured to: receive a second request to analyze a first patient not included in the plurality of patients, wherein the second request includes (i) first biological traits data associated with the first patient, (ii) first step count data associated with the first patient, and (iii) a first surgery type; retrieve, from the data repository, first analytics data based at least in part on the first biological traits data and the first surgery type, wherein the first analytics data is a subset of the analytics data stored in the data repository that corresponds to at least a portion of the first biological traits data and the first surgery type; determine, based at least in part on the first analytics data and the first step count data associated with the first patient, (a) a predicted surgical efficacy score associated with performing a first surgery of the first surgery type on the first patient and (b) a predicted pattern of post-surgery recovery associated with performing the first surgery on the first patient; and output a report associated with the first patient, wherein the report indicates at least the predicted surgical efficacy score and the predicted pattern of recovery.

EI 2: The system of EI 1, wherein the surgical efficacy score is calculated by dividing a first average value of the second step count data over the second temporal window by a second average value of the first step count data over the first temporal window.

EI 3: The system of EI 1, wherein the predicted pattern of post-surgery recovery is determined by aggregating a post-operative portion of the step count data of a subset of the plurality of patients that share a set of the same biological traits of the first patient.

EI 4: The system of EI 1, wherein the data analysis service is further configured to: determine the predicted surgical efficacy score for each of a plurality of surgeries including the first surgery; and output a recommendation for the first surgery based at least in part on (i) the predicted surgical efficacy score associated with the first surgery being the highest out of the plurality of surgeries, and (ii) the predicted surgical efficacy score associated with the first surgery indicating that the first surgery is predicted to result in at least a threshold level of mobility improvement for the first patient.

EI 5: The system of EI 1, wherein the step count data comprises, for a given patient of the plurality of patients, a number of steps estimated to be taken by the given patient based on sensor data captured by one or more sensors of a smartphone associated with the given patient, wherein the one or more sensors include one or more of an accelerometer, a gyroscope, a global positioning system (GPS) sensor, a compass, a magnetometer, or a barometer.

EI 6: The system of EI 1, wherein the step count data is collected by a mobile application installed on each of the plurality of respective user computing devices associated with the plurality of patients and transmitted to a data repository accessible by the data analysis service.

EI 7: The system of EI 1, wherein the data analysis service is further configured to: identify a first subset of the analytics data corresponding to a first subset of patients of the plurality of patients who have undergone the first surgery and are associated with a first set of biological traits; identify a second subset of the analytics data corresponding to a second subset of patients of the plurality of patients who have undergone the first surgery and are associated with a second set of biological traits different from the first set of biological traits; and output an aggregate report including (i) a first surgical efficacy score associated with the first surgery for the first subset of patients associated with the first set of biological traits, and (ii) a second surgical efficacy score associated with the first surgery for the second subset of patients associated with the second set of biological traits.

EI 8: The system of EI 1, wherein the data analysis service is further configured to: identify a first subset of the analytics data corresponding to a first subset of patients of the plurality of patients who have undergone the first surgery and are associated with a first set of biological traits; identify a second subset of the analytics data corresponding to a second subset of patients of the plurality of patients who have undergone a second surgery different from the first surgery and are associated with the first set of biological traits; and output an aggregate report including (i) a first surgical efficacy score associated with the first surgery for the first subset of patients associated with the first set of biological traits, and (ii) a second surgical efficacy score associated with the second surgery for the first subset of patients associated with the first set of biological traits.

EI 9: A computer-implemented method for providing analytics relating to patients and medical interventions, the method comprising: receiving a first request to analyze a plurality of patients, wherein the first request includes (i) biological traits data associated with the plurality of patients, (i) activity data associated with the plurality of patients, and (iii) medical intervention data associated with the plurality of patients; for each respective patient of the plurality of patients: identifying a set of temporal windows based at least in part on the activity data associated with the respective patient, wherein the set of temporal windows includes at least (i) a first temporal window prior to a medical intervention date associated with the respective patient, and (ii) a second temporal window subsequent to the medical intervention date; generating analytics data including a medical intervention efficacy score based at least in part on a comparison of first activity data associated with the first temporal window and second activity data associated with the second temporal window; and storing the analytics data in association with (a) at least a portion of the biological traits data associated with the respective patient and (b) at least a portion of the medical intervention data associated with the respective patient, receiving a second request to analyze a first patient, wherein the second request includes (i) first biological traits data associated with the first patient, (ii) first activity data associated with the first patient, and (iii) first medical intervention data; retrieving first analytics data based at least in part on the first biological traits data and the first medical intervention data, wherein the first analytics data is a subset of the analytics data generated based on the activity data associated with the plurality of patients that corresponds to at least a portion of the first biological traits data and the first medical intervention data; determining, based at least in part on the first analytics data and the first activity data associated with the first patient, (a) a predicted medical intervention efficacy score associated with performing a first medical intervention associated with the first medical intervention data on the first patient and (b) a predicted pattern of post-intervention recovery associated with performing the first medical intervention on the first patient; and outputting a report associated with the first patient, wherein the report indicates at least the predicted medical intervention efficacy score and the predicted pattern of recovery.

EI 10: The computer-implemented method of EI 9, wherein the activity data includes one or more of step count, step size, distance traveled, or flights of stairs climbed.

EI 11: The computer-implemented method of EI 9, wherein the medical intervention data includes one or more of a medical practitioner, a medical intervention date, a medical device used, a medical device manufacturer, a medical intervention duration, or a medical intervention time of day.

EI 12: The computer-implemented method of EI 9, wherein the medical intervention efficacy score is calculated by dividing a first average value of the second activity data over the second temporal window by a second average value of the first activity data over the first temporal window.

EI 13: The computer-implemented method of EI 9, wherein the predicted pattern of post-intervention recovery is determined by aggregating a post-operative portion of the activity data of a subset of the plurality of patients that share a set of the same biological traits of the first patient.

EI 14: The computer-implemented method of EI 9, further comprising: determining the predicted medical intervention efficacy score for each of a plurality of medical interventions associated with the first medical intervention data, wherein the plurality of medical interventions includes the first medical intervention; and outputting a recommendation for the first medical intervention based at least in part on (i) the predicted medical intervention efficacy score associated with the first medical intervention being the highest out of the plurality of medical interventions, and (ii) the predicted medical intervention efficacy score associated with the first medical intervention indicating that the first medical intervention is predicted to result in at least a threshold level of mobility improvement for the first patient.

EI 15: The computer-implemented method of EI 9, further comprising: identifying a first subset of the analytics data corresponding to a first subset of patients of the plurality of patients who have undergone the first medical intervention and are associated with a first set of biological traits; identifying a second subset of the analytics data corresponding to a second subset of patients of the plurality of patients who have undergone a second medical intervention different from the first medical intervention and are associated with the first set of biological traits; and outputting an aggregate report including (i) a first medical intervention efficacy score associated with the first medical intervention for the first subset of patients associated with the first set of biological traits, and (ii) a second medical intervention efficacy score associated with the second medical intervention for the first subset of patients associated with the first set of biological traits.

EI 16: A non-transitory computer readable medium storing instructions that, when executed by a computing system, cause the computing system to perform operations comprising: receiving a first request to analyze a plurality of patients, wherein the first request includes (i) biological traits data associated with the plurality of patients, (i) activity data associated with the plurality of patients, and (iii) medical intervention data associated with the plurality of patients; for each respective patient of the plurality of patients: identifying a set of temporal windows based at least in part on the activity data associated with the respective patient, wherein the set of temporal windows includes at least (i) a first temporal window prior to a medical intervention date associated with the respective patient, and (ii) a second temporal window subsequent to the medical intervention date; generating analytics data including a medical intervention efficacy score based at least in part on a comparison of first activity data associated with the first temporal window and second activity data associated with the second temporal window; and storing the analytics data in association with (a) at least a portion of the biological traits data associated with the respective patient and (b) at least a portion of the medical intervention data associated with the respective patient, receiving a second request to analyze a first patient, wherein the second request includes (i) first biological traits data associated with the first patient, (ii) first activity data associated with the first patient, and (iii) first medical intervention data; retrieving first analytics data based at least in part on the first biological traits data and the first medical intervention data, wherein the first analytics data is a subset of the analytics data generated based on the activity data associated with the plurality of patients that corresponds to at least a portion of the first biological traits data and the first medical intervention data; determining, based at least in part on the first analytics data and the first activity data associated with the first patient, (a) a predicted medical intervention efficacy score associated with performing a first medical intervention associated with the first medical intervention data on the first patient and (b) a predicted pattern of post-intervention recovery associated with performing the first medical intervention on the first patient; and outputting a report associated with the first patient, wherein the report indicates at least the predicted medical intervention efficacy score and the predicted pattern of recovery.

EI 17: The non-transitory computer readable medium of EI 16, wherein the medical intervention efficacy score is calculated by dividing a first average value of the second activity data over the second temporal window by a second average value of the first activity data over the first temporal window.

EI 18: The non-transitory computer readable medium of EI 16, wherein the predicted pattern of post-intervention recovery is determined by aggregating a post-operative portion of the activity data of a subset of the plurality of patients that share a set of the same biological traits of the first patient.

EI 19: The non-transitory computer readable medium of EI 16, storing further instructions that, when executed by the computing system, cause the computing system to perform operations comprising: determining the predicted medical intervention efficacy score for each of a plurality of medical interventions associated with the first medical intervention data, wherein the plurality of medical interventions includes the first medical intervention; and outputting a recommendation for the first medical intervention based at least in part on (i) the predicted medical intervention efficacy score associated with the first medical intervention being the highest out of the plurality of medical interventions, and (ii) the predicted medical intervention efficacy score associated with the first medical intervention indicating that the first medical intervention is predicted to result in at least a threshold level of mobility improvement for the first patient.

EI 20: The non-transitory computer readable medium of EI 16, storing further instructions that, when executed by the computing system, cause the computing system to perform operations comprising: identifying a first subset of the analytics data corresponding to a first subset of patients of the plurality of patients who have undergone the first medical intervention and are associated with a first set of biological traits; identifying a second subset of the analytics data corresponding to a second subset of patients of the plurality of patients who have undergone a second medical intervention different from the first medical intervention and are associated with the first set of biological traits; and outputting an aggregate report including (i) a first medical intervention efficacy score associated with the first medical intervention for the first subset of patients associated with the first set of biological traits, and (ii) a second medical intervention efficacy score associated with the second medical intervention for the first subset of patients associated with the first set of biological traits.

EI 21: A novel system and method to capture and transfer data from smartphones to a secure, encrypted, HIPAA-compliant network, comprising: automated de-identification of the personal health information (PHI) and assignment of unique identifier to each patient. This will ensure data security so that PHI is protected and even if breached, a hacker will not be able to match the medical history data back to individual patient in our database; and continuous data collection and processing allow for organized data visualization for numerous patients. The database will be constantly updated as well as new patients will sign up and download the mobile application.

EI 22: An ORBIT scoring system based on physical function of an user, wherein the scoring system ranges from −15 to 25, with higher score representing higher level of physical activity, wherein the ORBIT scoring system is a weighted scoring system with two components: temporal and gradient. Temporal grade is based on time to exceed baseline physical activity level from surgery, and gradient is graded based on the amount of increase or decrease in physical activity level compared to the baseline activity level, wherein ORBIT is a novel score calculated from the smartphone accelerometer data that is constantly being collected and stored using each device's algorithm (Apple iPhone), and wherein after physical activity data is imported from participant's cellular device, five parameters (SPD, DPD, ACB, SM, FC) are collected and organized into daily, weekly and monthly averages. Based on these data, ORBIT score is calculated for each patient and compared against conventional PROM (ODI, NDI, PROMIS) to determine either convergence or divergence, wherein ORBIT represents temporally continuous variable as opposed to PROM which is calculated at a single time point when the patient fills out a survey, thus allowing early detection of improvement or worsening during patient's recovery from surgery, which may alert the patient or the treating physician and trigger a close monitoring or follow-up, and wherein the present disclosure allows for real-time, continuously updated, objective, reliable, accurate and consistent assessment of patient's progress through surgical intervention such that this method for objective outcome measures may cause a fundamental paradigm shift towards value-based reimbursement model for Medicare/Medicaid/private insurance companies and away from traditional fee-for-service model.

EI 23: Supervised machine learning algorithm (MLA) that will be able to predict a user's future activity level based on historical activity data, demographic and relevant medical history, wherein the MLA can be trained by inputting clinical variables and relevant medical history to predict future outcomes for those patients who has not undergone surgery yet, wherein MLA will calculate future physical activity levels (SPD, DPD, ACB, SM, FC) of the patient based on pre-op baseline physical activity levels, baseline demographics such as age, sex, BMI, medical history, type of surgery and invasiveness of surgery, wherein based on predicted SPD, DPD, ACB, SM, FC, predicted ORBIT will be calculated for each patient based on different types of surgery (e.g. microdiscectomy, fusion, open versus minimally invasive spine surgery), and wherein based on these predictions, a clinician and a patient can decide which type of surgery is best suited for each patient.

Terminology

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

The processes described herein or illustrated in the figures of the present disclosure may begin in response to an event, such as on a predetermined or dynamically determined schedule, on demand when initiated by a user or system administrator, or in response to some other event. When such processes are initiated, a set of executable program instructions stored on one or more non-transitory computer-readable media (e.g., hard drive, flash memory, removable media, etc.) may be loaded into memory (e.g., RAM) of a server or other computing device. The executable instructions may then be executed by a hardware-based computer processor of the computing device. In some embodiments, such processes or portions thereof may be implemented on multiple computing devices and/or multiple processors, serially or in parallel.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multithreaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the scope of the disclosure. As can be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A system for providing analytics relating to patients and surgeries, the system comprising:
    a data repository storing analytics data associated with one or more patients; and
    a data analysis service comprising computer hardware, wherein the data analysis service is configured to at least:
        receive a first request to analyze a plurality of patients, wherein the first request includes (i) biological traits data associated with the plurality of patients, (i) step count data generated by a plurality of respective user computing devices associated with the plurality of patients, and (iii) surgery data associated with the plurality of patients; and
        for each respective patient of the plurality of patients:
            identify, based at least in part on the step count data associated with the respective patient exhibiting a first threshold level of change prior to a surgery date associated with the respective patient, a first pre-operative temporal window and a second pre-operative temporal window different from the first pre-operative temporal window;
            identify, based at least in part on the step count data associated with the respective patient exhibiting a second threshold level of change subsequent to the surgery date associated with the respective patient, a first post-operative temporal window and a second post-operative temporal window different from the first post-operative temporal window, wherein the second threshold level of change is different from the first threshold level of change; and
            train a prediction model usable to generate predictions for surgical efficacy and pattern of post-surgery recovery for subsequent patients by at least:
                generating a surgical efficacy score based at least in part on one or both of the first pre-operative temporal window and the second pre-operative temporal window and one or both of the first post-operative temporal window and the second post-operative temporal window; and
                storing the surgical efficacy score in association with (a) at least a portion of the biological traits data associated with the respective patient and (b) at least a portion of the surgery data associated with the respective patient, such that the surgical efficacy score associated with the respective patient is retrievable by the trained prediction model in a biological-trait-specific and surgery-specific manner and usable to generate subsequent predictions for surgical efficacy and pattern of post-surgery recovery in a standardized manner,
        wherein the data analysis service is further configured to:

receive a second request to analyze a first patient not included in the plurality of patients, wherein the second request includes (i) first biological traits data associated with the first patient, (ii) first step count data associated with the first patient, and (iii) a first surgery type;

use the trained prediction model to at least:
retrieve, from the data repository, first analytics data based at least in part on the first biological traits data and the first surgery type, wherein the first analytics data is a subset of the analytics data stored in the data repository that corresponds to at least a portion of the first biological traits data and the first surgery type; and generate, based at least in part on the first analytics data and the first step count data associated with the first patient, (a) a predicted surgical efficacy score associated with performing a first surgery of the first surgery type on the first patient and (b) a predicted pattern of post-surgery recovery associated with performing the first surgery on the first patient; and output a report associated with the first patient, wherein the report indicates at least the predicted surgical efficacy score and the predicted pattern of recovery.

2. The system of claim 1, wherein the surgical efficacy score is calculated by dividing a first average value of the second step count data over the second temporal window by a second average value of the first step count data over the first temporal window.

3. The system of claim 1, wherein the predicted pattern of post- surgery recovery is determined by aggregating a post-operative portion of the step count data of a subset of the plurality of patients that share a set of the same biological traits of the first patient.

4. The system of claim 1, wherein the data analysis service is further configured to:
determine the predicted surgical efficacy score for each of a plurality of surgeries including the first surgery; and
output a recommendation for the first surgery based at least in part on (i) the predicted surgical efficacy score associated with the first surgery being the highest out of the plurality of surgeries, and (ii) the predicted surgical efficacy score associated with the first surgery indicating that the first surgery is predicted to result in at least a threshold level of mobility improvement for the first patient.

5. The system of claim 1, wherein the step count data comprises, for a given patient of the plurality of patients, a number of steps estimated to be taken by the given patient based on sensor data captured by one or more sensors of a smartphone associated with the given patient, wherein the one or more sensors include one or more of an accelerometer, a gyroscope, a global positioning system (GPS) sensor, a compass, a magnetometer, or a barometer.

6. The system of claim 1, wherein the step count data is collected by a mobile application installed on each of the plurality of respective user computing devices associated with the plurality of patients and transmitted to a data repository accessible by the data analysis service.

7. The system of claim 1, wherein the data analysis service is further configured to:
identify a first subset of the analytics data corresponding to a first subset of patients of the plurality of patients who have undergone the first surgery and are associated with a first set of biological traits;
identify a second subset of the analytics data corresponding to a second subset of patients of the plurality of patients who have undergone the first surgery and are associated with a second set of biological traits different from the first set of biological traits; and
output an aggregate report including (i) a first surgical efficacy score associated with the first surgery for the first subset of patients associated with the first set of biological traits, and (ii) a second surgical efficacy score associated with the first surgery for the second subset of patients associated with the second set of biological traits.

8. The system of claim 1, wherein the data analysis service is further configured to:
identify a first subset of the analytics data corresponding to a first subset of patients of the plurality of patients who have undergone the first surgery and are associated with a first set of biological traits;
identify a second subset of the analytics data corresponding to a second subset of patients of the plurality of patients who have undergone a second surgery different from the first surgery and are associated with the first set of biological traits; and
output an aggregate report including (i) a first surgical efficacy score associated with the first surgery for the first subset of patients associated with the first set of biological traits, and (ii) a second surgical efficacy score associated with the second surgery for the first subset of patients associated with the first set of biological traits.

9. A computer-implemented method for providing analytics relating to patients and medical interventions, the method comprising:
receiving a first request to analyze a plurality of patients, wherein the first request includes (i) biological traits data associated with the plurality of patients, (i) activity data associated with the plurality of patients, and (iii) medical intervention data associated with the plurality of patients;

for each respective patient of the plurality of patients:
identifying, based at least in part on the activity data associated with the respective patient exhibiting a first threshold level of change prior to a medical intervention date associated with the respective patient, a first pre-operative temporal window and a second pre-operative temporal window different from the first pre-operative temporal window;
identifying, based at least in part on the activity data associated with the respective patient exhibiting a second threshold level of change subsequent to the medical intervention date associated with the respective patient, a first post-operative temporal window and a second post- operative temporal window different from the first post-operative temporal window, wherein the second threshold level of change is different from the first threshold level of change; and
training a prediction model usable to generate predictions for medical intervention efficacy and pattern of post-intervention recovery for subsequent patients by at least:
generating analytics data including a medical intervention efficacy score based at least in part on one or both of the first pre-operative temporal window and the second pre-operative temporal window and one or both of the first post-operative temporal window and the second post-operative temporal window and storing the analytics data in association with (a) at least a portion of the biological traits data associated with the respective patient and (b) at least a portion of the medical intervention data associated with the respective patient, such that the medical intervention efficacy score associated with the respective patient is retrievable by the trained prediction model in a biological-trait-specific and medical-intervention-specific manner and usable to generate subsequent predictions for medical intervention efficacy and pattern of post-intervention recovery in a more standardized manner, receiving a second request to analyze a first patient, wherein the second request includes (i) first biological traits data associated with the first patient, (ii) first activity data associated with the first patient, and (iii) first medical intervention data;

using the trained prediction model to at least:
retrieve first analytics data based at least in part on the first biological traits data and the first medical intervention data, wherein the first analytics data is a subset of the analytics data generated based on the activity data associated with the plurality of patients that corresponds to at least a portion of the first biological traits data and the first medical intervention data; and generate, based at least in part on the first analytics data and the first activity data associated with the first patient, (a) a predicted medical intervention efficacy score associated with performing a first medical intervention associated with the first medical intervention data on the first patient and (b) a predicted pattern of post-intervention recovery associated with performing the first medical intervention on the first patient; and outputting a report associated with the first patient, wherein the report indicates at least the predicted medical intervention efficacy score and the predicted pattern of recovery.

10. The computer-implemented method of claim 9, wherein the activity data includes one or more of step count, step size, distance traveled, or flights of stairs climbed.

11. The computer-implemented method of claim 9, wherein the medical intervention data includes one or more of a medical practitioner, a medical intervention date, a medical device used, a medical device manufacturer, a medical intervention duration, or a medical intervention time of day.

12. The computer-implemented method of claim 9, wherein the medical intervention efficacy score is calculated by dividing a first average value of the second activity data over the second temporal window by a second average value of the first activity data over the first temporal window.

13. The computer-implemented method of claim 9, wherein the predicted pattern of post-intervention recovery is determined by aggregating a post- operative portion of the activity data of a subset of the plurality of patients that share a set of the same biological traits of the first patient.

14. The computer-implemented method of claim 9, further comprising:
determining the predicted medical intervention efficacy score for each of a plurality of medical interventions associated with the first medical intervention data, wherein the plurality of medical interventions includes the first medical intervention; and
outputting a recommendation for the first medical intervention based at least in part on (i) the predicted medical intervention efficacy score associated with the first medical intervention being the highest out of the plurality of medical interventions, and (ii) the predicted medical intervention efficacy score associated with the first medical intervention indicating that the first medical intervention is predicted to result in at least a threshold level of mobility improvement for the first patient.

15. The computer-implemented method of claim 9, further comprising:
identifying a first subset of the analytics data corresponding to a first subset of patients of the plurality of patients who have undergone the first medical intervention and are associated with a first set of biological traits;
identifying a second subset of the analytics data corresponding to a second subset of patients of the plurality of patients who have undergone a second medical intervention different from the first medical intervention and are associated with the first set of biological traits; and
outputting an aggregate report including (i) a first medical intervention efficacy score associated with the first medical intervention for the first subset of patients associated with the first set of biological traits, and (ii) a second medical intervention efficacy score associated with the second medical intervention for the first subset of patients associated with the first set of biological traits.

16. A non-transitory computer-readable medium storing instructions that, when executed by a computing system, cause the computing system to perform operations comprising:
receiving a first request to analyze a plurality of patients, wherein the first request includes (i) biological traits data associated with the plurality of patients, (i) activity data associated with the plurality of patients, and (iii) medical intervention data associated with the plurality of patients;

for each respective patient of the plurality of patients:
identifying, based at least in part on the activity data associated with the respective patient exhibiting a first threshold level of change prior to a medical intervention date associated with the respective patient, a first pre-operative temporal window and a second pre-operative temporal window different from the first pre-operative temporal window;

identifying, based at least in part on the activity data associated with the respective patient exhibiting a second threshold level of change subsequent to the medical intervention date associated with the respective patient, a first post-operative temporal window and a second post-operative temporal window different from the first post-operative temporal window, wherein the second threshold level of change is different from the first threshold level of change; and training a prediction model usable to generate predictions for medical intervention efficacy and pattern of post-intervention recovery for subsequent patients by at least:
generating analytics data including a medical intervention efficacy score based at least in part on one or both of the first pre-operative temporal window and the second pre-operative temporal window and one or both of the first post-operative temporal window and the second post-operative temporal window; and storing the analytics data in association with (a) at least a portion of the biological traits data associated with the respective patient and (b) at least a portion of the medical intervention data associated with the respective patient, such that the medical intervention efficacy score associated with the respective patient is retrievable by the trained prediction model in a biological-trait-specific and medical-intervention-specific manner and usable to generate subsequent predictions for medical intervention efficacy and pattern of post-intervention recovery in a more standardized manner, receiving a second request to analyze a first patient, wherein the second request includes (i) first biological traits data associated with the first patient, (ii) first activity data associated with the first patient, and (iii) first medical intervention data;

using the trained prediction model to at least:
retrieve first analytics data based at least in part on the first biological traits data and the first medical intervention data, wherein the first analytics data is a subset of the analytics data generated based on the activity data associated with the plurality of patients that corresponds to at least a portion of the first biological traits data and the first medical intervention data; and generate, based at least in part on the first analytics data and the first activity data associated with the first patient, (a) a predicted medical intervention efficacy score associated with performing a first medical intervention associated with the first medical intervention data on the first patient and (b) a predicted pattern of post-intervention recovery associated with performing the first medical intervention on the first patient; and outputting a report associated with the first patient, wherein the report indicates at least the predicted medical intervention efficacy score and the predicted pattern of recovery.

17. The non-transitory computer-readable medium of claim 16, wherein the medical intervention efficacy score is calculated by dividing a first average value of the second activity data over the second temporal window by a second average value of the first activity data over the first temporal window.

18. The non-transitory computer-readable medium of claim 16, wherein the predicted pattern of post-intervention recovery is determined by aggregating a post-operative portion of the activity data of a subset of the plurality of patients that share a set of the same biological traits of the first patient.

19. The non-transitory computer-readable medium of claim 16, storing further instructions that, when executed by the computing system, cause the computing system to perform operations comprising:

determining the predicted medical intervention efficacy score for each of a plurality of medical interventions associated with the first medical intervention data, wherein the plurality of medical interventions includes the first medical intervention; and outputting a recommendation for the first medical intervention based at least in part on (i) the predicted medical intervention efficacy score associated with the first medical intervention being the highest out of the plurality of medical interventions, and (ii) the predicted medical intervention efficacy score associated with the first medical intervention indicating that the first medical intervention is predicted to result in at least a threshold level of mobility improvement for the first patient.

20. The non-transitory computer-readable medium of claim 16, storing further instructions that, when executed by the computing system, cause the computing system to perform operations comprising:

identifying a first subset of the analytics data corresponding to a first subset of patients of the plurality of patients who have undergone the first medical intervention and are associated with a first set of biological traits;

identifying a second subset of the analytics data corresponding to a second subset of patients of the plurality of patients who have undergone a second medical intervention different from the first medical intervention and are associated with the first set of biological traits; and outputting an aggregate report including (i) a first medical intervention efficacy score associated with the first medical intervention for the first subset of patients associated with the first set of biological traits, and (ii) a second medical intervention efficacy score associated with the second medical intervention for the first subset of patients associated with the first set of biological traits.

* * * * *